(12) United States Patent
Ricard et al.

(10) Patent No.: US 10,576,028 B2
(45) Date of Patent: *Mar. 3, 2020

(54) AQUEOUS COMPOSITION FOR CARING FOR AND/OR MAKING UP KERATIN MATERIALS COMPRISING MICROCAPSULES ENCAPSULATING AN OILY DISPERSION OF AT LEAST ONE REFLECTIVE AGENT

(71) Applicant: L'OREAL, Paris (FR)

(72) Inventors: Audrey Ricard, Chevilly Larue (FR); Danny Goldstein, Northern Galilee (IL)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/757,595

(22) PCT Filed: Sep. 3, 2015

(86) PCT No.: PCT/EP2015/070174
§ 371 (c)(1),
(2) Date: Mar. 5, 2018

(87) PCT Pub. No.: WO2017/036538
PCT Pub. Date: Mar. 9, 2017

(65) Prior Publication Data
US 2019/0000728 A1    Jan. 3, 2019

(51) Int. Cl.
| A61K 8/11 | (2006.01) |
|---|---|
| A61Q 1/02 | (2006.01) |
| A61K 8/20 | (2006.01) |
| A61K 8/02 | (2006.01) |
| A61K 8/29 | (2006.01) |

(52) U.S. Cl.
CPC .............. *A61K 8/11* (2013.01); *A61K 8/0254* (2013.01); *A61K 8/20* (2013.01); *A61K 8/29* (2013.01); *A61Q 1/02* (2013.01); *A61K 2800/43* (2013.01)

(58) Field of Classification Search
CPC ... A61K 8/11; A61K 1/02; A61K 8/20; A61K 8/0254; A61K 8/29
See application file for complete search history.

(56) References Cited

U.S. PATENT DOCUMENTS

| 4,879,175 A | 11/1989 | Ugro, Jr. |
|---|---|---|
| 6,932,984 B1 | 8/2005 | Babtsov et al. |
| 2005/0048014 A1 | 3/2005 | Linz et al. |
| 2006/0051425 A1* | 3/2006 | Kvitnitsky .......... A61K 9/0014 424/490 |
| 2006/0292193 A1 | 12/2006 | Lee et al. |
| 2007/0220686 A1 | 9/2007 | Jeanne-Rose et al. |
| 2009/0035365 A1 | 2/2009 | Popplewell et al. |
| 2012/0269752 A1* | 10/2012 | Ozee ..................... A61K 8/042 424/63 |
| 2014/0335138 A1 | 11/2014 | Goldstein et al. |

FOREIGN PATENT DOCUMENTS

| EP | 0 225 799 A2 | 6/1987 |
|---|---|---|
| EP | 0 917 870 A1 | 5/1999 |
| WO | WO 2006/041658 A1 | 4/2006 |
| WO | WO 2013/106996 * | 7/2013 |
| WO | WO 2015/138319 A1 | 9/2015 |

OTHER PUBLICATIONS

International Search Report dated Feb. 9, 2016, in PCT/EP2015/070174 filed Sep. 3, 2015.

* cited by examiner

*Primary Examiner* — Shirley V Gembeh
(74) *Attorney, Agent, or Firm* — Oblon, McClelland, Maier & Neustadt, L.L.P.

(57) ABSTRACT

The present invention concerns a composition, in particular in the form of aqueous dispersion for caring for and/or making up keratin materials comprising, in a physiologically acceptable medium, a) one aqueous phase; and b) at least microcapsules comprising:—an inner core comprising at least a dispersion of at least one reflective agent, in particular bismuth oxychloride, in at least one oil, and—at least one outer shell formed of a wall-forming polymeric material surrounding the said core, the said outer shell comprising i) at least one wall-forming polymer, and ii) optionally at least one plasticizer and/or at least one opaque substance and/or at least one fatty acid salt. The present invention concerns also a cosmetic process for caring for and/or making up keratinic materials, comprising application on said keratinic materials in particular on the skin of a composition as above defined.

20 Claims, No Drawings

AQUEOUS COMPOSITION FOR CARING FOR AND/OR MAKING UP KERATIN MATERIALS COMPRISING MICROCAPSULES ENCAPSULATING AN OILY DISPERSION OF AT LEAST ONE REFLECTIVE AGENT

The present invention concerns a composition, in particular in the form of aqueous dispersion, for caring for and/or making up keratin materials comprising, in a physiologically acceptable medium,
   a) one aqueous phase; and
   b) at least microcapsules comprising:
      an inner core comprising at least a dispersion of at least one reflective agent, in particular bismuth oxychloride, in at least one oil, and
      at least one outer shell formed of a wall-forming polymeric material surrounding the said core, the said outer shell comprising
         i) at least one wall-forming polymer, and
         ii) optionally at least one plasticizer and/or at least one opaque substance and/or at least one fatty acid salt.

The present invention concerns also a cosmetic process for caring for and/or making up keratinic materials, comprising application on said keratinic materials in particular on the skin of a composition as above defined.

Consumers are looking for new skin care and/or make up products to improve the appearance of keratin materials and especially the skin, in particular the surface appearance (visible and/or tactile) and/or skin tone including brightness or a light effect to the skin with a natural glow and advantageously a healthy glow. The consumers increasingly reject the makeup products that, when applied to the face, leading to a dull and bland results. They want, instead, a bright makeup that gives luster. It is important also to find a good balance between the lightness and the coverage, dullness and color given by the pigments and fillers to cover, smooth and/or unifying skin dyschromias, relief imperfections such as pores, wrinkles and/or fine lines and/or scarring.

By 'light' or 'light effect' is meant according to the invention the reflection characteristic of light, diffuse reflection and continues on the skin. Indeed, the skin naturally reflects part of the incident light. The "light effect" according to the invention can increase this reflection, which provides the makeup rendering brighter, more sparkle.

For 'healthy glow', a natural skin coloring means, with an improvement of dull complexion (desaturating or chromatic effect and anti-dull completion).

The use of reflective agents as bismuth oxychloride (CI 77163) in cosmetic formulations is well-known and notably described in WO 2004/041234 and U.S. Pat. No. 7,033,614.

The use of reflective agents as bismuth oxychloride (CI 77163) as a powder or agglomerates is known in foundations as a charge to bring some sensory (soft). This compound can also bring a punctual and discontinuous satin effect, which in products such as fluids, or even compact powders can be perceived as a pearly shine. However, because of its capacity to absorb moisture and oils, bismuth oxychloride under powder form or agglomerate has a tendency to render white and to affect the final visual rendering of the product after application on the skin and the sensory properties such as freshness. In addition, the powder form requires industrial constraints of grinding to a finer particle size in order to obtain more bright, more sparkle.

To remedy these problems of whitening of final visual rendering and of particle size industrial constraint, it has been proposed to use bismuth oxychloride (CI 77163) as a bismuth oxychloride dispersion in a polar oil as for instance, in U.S. Patent Application having Publication No. 2012/0269752.

However, this oily dispersion used in aqueous solutions has a tendency to modify and alter the fluidity and light-weight of the texture by the presence of the oil, to reduce the light effect and alter the natural glow, to alter the sensorial properties during and/or after application as the play time, the freshness, the smoothness, a non greasy feeling. Furthermore, the bismuth oxychloride oily dispersion has a tendency to give a too pearly shine in the mass which may be undesirable for greasy skins and dark skins.

In the prior art, in particular in the documents US2010095868, U.S. Pat. No. 7,622,132, WO09079135, EP1518903B1, it has been proposed to use a reflective agent in microcapsule as nacres pigments containing bismuth oxychloride or bismuth oxychloride.

In cosmetic formulations it is generally highly desirable to retain a cosmetically active agent that provides a visual effect within capsules before application thereof. Encapsulation of such agent is thought for in order to maintain a long term visual effect of the cosmetic formulation; to protect the encapsulated agent from interacting with other agents in the formulation; to mask the visual effect of the active agent before application; to maintain the stability of the active agent in a formulation and/or to release the encapsulated active agent only upon application. The effectiveness of protection/masking by single-layer microencapsulation depends on the chemical structure, molecular weight and physical properties of the microencapsulated ingredient.

Microparticles encapsulating a variety of cosmetically active agents, including colorants and/or pigments and other agents that provide a visual effect, have been described in the art.

U.S. Pat. Nos. 5,320,835 and 5,382,433 disclose "activable" dormant colored particles or pigments and cosmetic formulations comprising them and further comprising a colored base phase, and colorant entrapping substrate particles dispersed in said base phase. The encapsulated colorants are said to be released into the base phase when mechanical action is applied to the cosmetic formulation, and produce an intense shade in the color of the base phase, whereas the colorant entrapping substrate particles entrap the released colorants and produce a subtle shade in the color of the base phase. The encapsulated pigments are made by a coacervation method.

WO 98/5002 discloses similar color-sustainable base cosmetic formulations, further including volatile solvents to minimize the gritty feel of the microencapsulated material. The color obtained from the released encapsulated pigments is exactly the same as the color of the composition itself. Releasing provides renewed intensity of the original base color.

U.S. Pat. No. 5,380,485 discloses colored cosmetic compositions, comprising particulate fillers coated with polymer that is combined with colorants, and their application in decorative cosmetics.

U.S. Patent Application having Publication Nos. 2005/0031558 and 2005/0276774 disclose a personal care or cosmetic composition containing microparticles comprising a shatter resistant blend of distinct colorants microencapsulated within a polymer matrix, preferably a cross-linked polymer matrix that does not allow any of the entrapped colorant to be released even under prolonged use. The matrix polymer is preferably transparent or translucent such that the blend of encapsulated colorants provides the coloring of the cosmetic product itself and of the skin upon application of the cosmetic composition. The microparticles disclosed in U.S. Patent Application having Publication No. 2005/0276774 further contain secondary particles (i.e. hydrophobic polymers different from those of the matrix polymer) that are distributed throughout the matrix.

U.S. Pat. No. 4,756,906 discloses decorative cosmetic compositions containing a first colorant and microcapsules containing a solvated second colorant, different from the first colorant. Upon rupture of the microcapsules, the coloration of the encapsulated pigment is added into the composition thereby altering its color characteristics.

WO 2004/075679 discloses rigid, non-rupturable microcapsules containing a blend of at least two coloring agents and compositions comprising them, which do not change their color upon application onto the skin. The microcapsules are non-rupturable due to the use of cross-linked polymeric matrix comprising polymers that have a glass transition temperature (Tg) higher than 80° C.

U.S. Pat. No. 6,932,984 discloses single- and double-layer microcapsules and a method for microencapsulation of substances by the solvent removal method using non-chlorinated solvents. The method is based on physical processes which do not cause any change of original physical and/or chemical properties, biological activity, and safety of raw materials during the process.

U.S. Pat. No. 7,838,037 discloses double-layer and/or triple-layer microcapsules, designed to rupture by a slight mechanical action such as rubbing or pressing on the skin, and thereby immediately release their encapsulated content. These microcapsules are prepared by the solvent removal method using non-chlorinated solvents. This method affords physical stability to the microcapsules, high ability to entrap the active agents, protection of the active agents inside the microcapsules, and prevention of the diffusion of the microencapsulated active agents to the external water phase in a water-based preparation.

WO 2009/138978 discloses cosmetic compositions for dermal/topical application comprising double-layer, rupturable microcapsules which contain one or more microencapsulated colorants. When applied to the skin, such compositions produce an immediate color change effect indicating the delivery to the skin of the active substances contained in said compositions.

There is thus a need to find new aqueous compositions, in particular in the form of aqueous dispersion based on a reflective agent which do not have the drawbacks as mentioned above There is a need not to modify and alter the fluidity and lightweight of the texture by the presence of the oil, not to reduce the light effect and not to alter the natural glow, not to alter the sensorial properties during and/or after application as the play time, the freshness, the smoothness, a non greasy feeling. Furthermore, There is a need not to give a too pearly shine in the mass which may be undesirable for greasy skins and dark skins.

There is also the need to use in the said compositions of a reflective agent in an appropriate encapsulated form which may efficiently mask the visual effect of the reflective agent before application and/or release the encapsulated active agent only upon application.

The applicant has surprisingly discovered that this objective can be achieved with an aqueous composition, in particular in the form of aqueous dispersion, for caring for and/or making up keratin materials comprising, in a physiologically acceptable medium, a) one aqueous phase; and
b) at least microcapsules comprising:
an inner core comprising at least a dispersion of at least one reflective agent, in particular bismuth oxychloride, in at least one oil, and
at least one outer shell formed of a wall-forming polymeric material surrounding the said core, the said outer shell comprising
i) at least one wall-forming polymer, and
ii) optionally at least one plasticizer and/or at least one opaque substance and/or at least one fatty acid salt.

The microcapsules of the invention as described below, contain at least a dispersion of a reflective agent, in particular bismuth oxychloride, in at least one oil, and allow to encapsulate the said dispersion in high load (e.g., higher than 50%, 60% and even higher than 70%, of the total weight of the microcapsule. The said microcapsules, are stable during the manufacturing and storage processes, maintain the encapsulated oily dispersion of reflective agent inside the capsules with minimal or nullified leakage, and are rupturable under mild shear forces, thus enabling an immediate release of the encapsulated agent upon application of the microcapsules to the skin. The obtained microcapsules provided herewith may further provide a masking effect of the light reflectance of the reflective agent before rupture, if desired.

This discovery is the basis of the invention.

The present invention concerns a composition, in particular in the form of aqueous dispersion for caring and/or making up keratin materials comprising, in a physiologically acceptable medium, a) one aqueous phase; and
b) at least microcapsules comprising:
an inner core comprising at least a dispersion of at least one reflective agent, in particular bismuth oxychloride, in at least one oil, and
at least one outer shell formed of a wall-forming polymeric material surrounding the said core, the said outer shell comprising
i) at least one wall-forming polymer, and
ii) optionally at least one plasticizer and/or at least one opaque substance and/or at least one fatty acid salt.

Definitions

"Physiologically acceptable medium" means any medium compatible with the keratin materials, which has a color, a smell and a pleasant feel and which does not generate unacceptable discomfort (stinging, tautness or redness) liable to put the consumer from using this composition.

In the context of the present invention, the term "keratin materials" means the skin and especially areas like the face, cheeks, hands, body, legs, around the eyes, the eyelids and the lips.

In the context of the present invention, the term "aqueous dispersion" means an aqueous solution wherein are dispersed the microcapsules as above defined and optionally additives which are water-insoluble as additional fillers, coloring agents Microcapsules The microcapsules provided by the present embodiments are particles (e.g., generally spherical particles), which are generally closed structures containing at least an encapsulated (enveloped, entrapped) oily dispersion of a reflective agent, in particular bismuth oxychloride. The microcapsules generally have a core-shell structural feature, namely each microcapsule is comprised of a polymeric shell and a core that comprises at least one oily dispersion of reflective agent enveloped by the shell.

The shell of the microcapsule is typically applied as a wall-forming material and serves as a membrane for the encapsulated substance. In some embodiments, the outer shell exhibits some opacity, or otherwise a masking effect of the reflective agent, by virtue of inclusion of an opaque substance in the shell, optionally in combination with a fatty acid salt.

The outer shell may further comprise a plasticizer to control its hardness, and is designed such that the microcapsules are rupturable upon rubbing or pressing on the skin.

In some of any of the embodiments described herein, the microcapsules are single-layer microcapsules, comprising a single outer shell enveloping the inner core. In some other embodiments, the microcapsules are double-layer, or triple-layer, or multi-layer microcapsules, comprising additional one or more layers enveloping the shell that envelopes the inner core.

A multi-layer microcapsule is featured as comprising an inner core microcapsule comprising a core which comprises an oily dispersion of bismuth oxychloride, as described herein, being enveloped by a first shell comprised of a first wall-forming material, and at least one additional shell comprised of a second wall forming material enveloping said first shell, which can be regarded as enveloping a single-layer microcapsule as described herein (comprising the reflective agent-containing inner core and a first shell of a first wall-forming material).

Each shell in the multi-layered microcapsules is typically and independently applied as a wall-forming material (e.g., a first, second, third and so forth wall-forming materials forming the first, second, third, and so forth, outer shells, respectively), and serves as a membrane for the encapsulated substance. In some embodiments, one or more, or each, of the outer shells in the multi-layered microcapsules according to these embodiments is optionally opaque by virtue of an opaque substance comprised therein, and/or further contains a fatty acid salt, as described herein.

The microcapsules of the present embodiments, among other uses, are suitable for inclusion in topical, e.g., cosmetic, cosmeceutical and pharmaceutical (e.g., dermatological), applications. When applied to the skin, the microcapsules are capable of being ruptured upon application of shear forces such as rubbing and pressing on the skin, but they remain intact in the formulation itself before application. The microcapsules are hard enough to avoid destruction of the shells and realization of the content during production processes such as isolation/filtration, drying, sieving, etc., and/or during storage.

In some embodiments, the microcapsules encapsulating an oily dispersion of bismuth oxychloride as described herein are prepared by a solvent removal method, as described hereinunder and exemplified in the Examples section that follows.

In some embodiments, a mean size of the microcapsules as described herein is within a range of from 10 μm to 400 μm, more preferably from 50 μm to 350 μm, more particularly from 50 μm to 250 μm, advantageously from 90 μm to 250 μm, more advantageously from 100 μm to 200 μm.

Herein throughout, a "mean" size means an average size of the microcapsules. The size of the microcapsules may be measured by a Laser distribution size method and particularly by measuring the values D[50] and D[90].

D50 means the size of which 50% of the microcapsules do not exceed, and D90 means the size of which 90% of the microcapsules do not exceed.

In some of any of the embodiments described herein, the outer shell comprises, in addition to the wall-forming material, a fatty acid salt, and an opaque substance, as described herein.

According to some of any of the embodiments of the present invention, the microcapsules described herein exhibit masking of the luminous effect of the oily dispersion of bismuth oxychloride, as reflected by a positive shift (delta) of the lightness value (L*) determined in X-rite measurements.

According to some of any of the embodiments of the invention, a microcapsule as described herein is rupturable or breakable when applied to the skin; that is, a microcapsule as described herein remains intact in a formulation containing same and during industrial processes, but readily breaks when pressed of rubbed on the skin. The non-breakability of the microcapsules before topical application thereof is routinely assessed by monitoring (e.g., using a light microscope) the ability of the microcapsules in a basic cream or lotion to sustain their size and shape when subjected to low shear mixing at e.g., 40-600 (or 80-100) rpm for 5-10 minutes at room temperature and at 40° C. A change of less than 10% in the microcapsule size is indicative of the non-breakability of the microcapsules upon routine industrial processes.

The Inner Core:

The inner core in the microcapsules described herein comprises at least a dispersion of at least one reflective agent in at least one oil.

a) Reflective agent(s)

As used herein, a "reflective agent" describes an agent which increases the diffuse light reflection of a substrate onto which it is applied. A reflective agent as described herein is typically intended to increase the light reflection of keratinous substrates, particularly the skin, and more particularly facial skin.

According to some embodiments of the invention, a reflective agent may comprise, or be in a form of, particles, whereby the particles are characterized by dimensions and arrangement (e.g, a layered structure), and other physical and chemical features, which, when applied to a surface, cause reflection of incident light with a sufficient intensity that is visible to the naked eye. As a result, a reflective agent provides the substrate onto which it is applied points of brightness that contrast with their surroundings by appearing to shine.

In some embodiments, the reflective agent provides for a continuous diffuse reflection over the skin, and imparts a light effect or luminosity to facial skin when applied thereon.

A "light reflection" or "light effect" or "luminosity" or "luminous effect" as described herein, can be determined as described in the Examples section that follows.

An exemplary reflective agent is bismuth oxychloride.

Other exemplary reflective agents include, but are not limited to, inorganic nacres, particles with metallic glint, micas and other inorganic pigments, and combination thereof.

Inorganic pigments that are usable in the context of these embodiments of the present invention include, but are not limited to, titanium oxides, zirconium oxides, cerium oxides, zinc oxides, iron oxides, chromium oxides, ferric blue, manganese violet, ultramarine blue and chromium hydrate.

Additional pigments that are usable in the context of these embodiments of the present invention include, but are not limited to, pigment structures of the sericite/brown iron oxide/titanium dioxide/silica type, or of $BaSO_4/TiO_2/FeSO_3$ type, of silica/iron oxide type, or silica microspheres containing iron oxide.

The term "nacres" describes iridescent or non-iridescent colored particles, either of a natural origin (e.g., produced by certain molluscs in their shell) or synthesized, which exhibit a color effect by featuring optical interference. The term "nacres" is also referred to herein as "nacreous pigments".

Exemplary nacreous pigments include, but are not limited to, titanium mica coated with an iron oxide, titanium mica coated with bismuth oxychloride, titanium mica coated with chromium oxide, titanium mica coated with an organic dye and also nacreous pigments based on bismuth oxychloride. These may also be mica particles at the surface of which are superposed at least two successive layers of metal oxides and/or of organic colorants.

Additional exemplary nacres include, but are not limited to, natural mica coated with titanium oxide, with iron oxide, with natural pigment or with bismuth oxychloride.

Commercially available nacres include, for example, the Timica, Flamenco and Duochrome (mica-based) nacres sold by the company BASF, the Timiron nacres sold by the company Merck, the Prestige mica-based nacres sold by the company Eckart, the following nacres based on natural mica: Sunpearl from the company Sun Chemical, KTZ from the company Kobo and Sunprizma from the company Sun Chemical, the Sunshine and Sunprizma nacres based on synthetic mica sold by the company Sun Chemical, and the Timiron Synwhite nacres based on synthetic mica sold by the company MERCK.

More particular examples include gold-colored nacres sold especially by the company BASF under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the names Bronze fine (17384) (Colorona) and Bronze (17353) (Colorona) and by the company BASF under the name Super bronze (Cloisonne); the orange nacres sold especially by the company BASF under the names Orange 363C (Cloisonne) and Orange MCR 101 (Cosmica) and by the company Merck under the names Passion orange (Colorona) and Matte orange (17449) (Microna); the brown-tinted nacres sold especially by the company BASF under the names Nuantique copper 340X6 (Cloisonne) and Brown CL4509 (Chromalite); the nacres with a copper tint sold especially by the company BASF under the name Copper 340A (Timica); the nacres with a red tint sold especially by the company Merck under the name Sienna fine (17386) (Colorona); the nacres with a yellow tint sold especially by the company BASF under the name Yellow (4502) (Chromalite); the red-tinted nacres with a golden tint sold especially by the company BASF under the name Sunstone G012 (Gemtone); the pink nacres sold especially by the company BASF under the name Tan opale G005 (Gemtone); the black nacres with a golden tint sold especially by the company BASF under the name Nu antique bronze 240 AB (Timica); the blue nacres sold especially by the company Merck under the name Matte blue (17433) (Microna); the white nacres with a silvery tint sold especially by the company Merck under the name Xirona Silver; and the golden-green pinkish-orange nacres sold especially by the company Merck under the name Indian summer (Xirona), and mixtures thereof.

Exemplary particles with a metallic glint which are usable in the context of the present embodiments include, but are not limited to, particles of at least one metal and/or of at least one metal derivative, particles comprising a single-material or multi-material organic or inorganic substrate, at least partially coated with at least one layer with a metallic glint comprising at least one metal and/or at least one metal oxide, metal halide or metal sulfide, and mixtures of said particles.

Exemplary metals that may be present in such particles include, but are not limited to, Ag, Au, Cu, Al, Ni, Sn, Mg, Cr, Mo, Ti, Zr, Pt, Va, Rb, W, Zn, Ge, Te and Se, and mixtures or alloys thereof, preferably Ag, Au, Cu, Al, Zn, Ni, Mo and Cr and mixtures or alloys thereof.

Exemplary particles with metallic glint include, but are not limited to, aluminum particles, such as those sold under the names Starbrite 1200 EAC® by the company Siberline and Metalure® by the company Eckart; particles made of metal powders of copper or of alloy mixtures such as the references 2844 sold by the company Radium Bronze, metallic pigments, for instance aluminium or bronze, such as those sold under the names Rotosafe 700 from the company Eckart, silica-coated aluminium particles sold under the name Visionaire Bright Silver from the company Eckart, and metal alloy particles, for instance the silica-coated bronze (alloy of copper and zinc) powders sold under the name Visionaire Bright Natural Gold from the company Eckart.

Other particles are those comprising a glass substrate such as those sold by the company Nippon Sheet Glass under the names Microglass Metashine, Xirona from the company Merck, Ronastar from the company Merck, Reflecks from the company BASF and Mirage from the company BASF.

Additional exemplary reflective agents include, goniochromatic coloring agents such as, for example, multilayer interference structures and liquid-crystal coloring agents.

Other reflective agents would be readily recognized by those skilled in the art.

According a preferred embodiment of the invention, reflective agent is bismuth oxychloride.

b) Oil(s) used in the Dispersion

According to the present invention, the term "oil" means a water-immiscible non-aqueous compound that is liquid at room temperature (25° C.) and at atmospheric pressure (760 mmHg).

According to a preferred embodiment, the oil is a polar oil.

The term "polar oil", as used herein, refers to any oil having, at 25° C., a solubility parameter $\delta_d$ characteristic of dispersive interactions of greater than 16 and a solubility parameter $\delta_p$ characteristic of polar interactions strictly greater than 0. The solubility parameters $\delta_d$ and $\delta_p$ are defined according to the Hansen classification.

For example, these polar oils may be chosen from esters, triglycerides and ethers.

The definition and calculation of the solubility parameters in the Hansen three-dimensional solubility space are described in the paper by C. M. Hansen: "The three dimensional solubility parameters", J. Paint Technol. 39, 105 (1967).

According to this Hansen space:
$\delta_D$ characterizes the London dispersion forces derived from the formation of dipoles induced during molecular impacts;
$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a=(\delta_p^2+\delta_h^2)^{1/2}$.

The parameters $\delta_p$, $\delta_h$, $\delta_D$ and $\delta_a$ are expressed in $(J/cm^3)^{1/2}$.

The polar oils will preferably be chosen from oils having $\delta_a>6$.

These polar oils may be of plant, mineral or synthetic origin.

The polar oils will preferably be chosen from non-volatile polar hydrocarbon-based oils.

The term "polar hydrocarbon-based oil" means a polar oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

The term "non-volatile oil" means an oil that remains on the skin or the keratin fiber at room temperature and atmospheric pressure for at least several hours, and that especially has a vapour pressure of less than $10^{-3}$ mmHg (0.13 Pa).

The non-volatile polar hydrocarbon-based oil may be chosen especially from the following oils:

hydrocarbon-based polar oils such triglycerides consisting of fatty acid esters of glycerol, in particular the fatty acids of which may have chain lengths ranging from $C_4$ to $C_{36}$, and especially from $C_{18}$ to $C_{36}$, these oils possibly being linear or branched, and saturated or unsaturated; these oils may especially be heptanoic or octanoic triglycerides, wheatgerm oil, sunflower oil, grapeseed oil, sesame seed oil (820.6 g/mol), corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passionflower oil or musk rose oil; or alternatively caprylic/capric acid triglycerides, for instance those sold by the company Stéarineries Dubois or those sold under the names Miglyol 810®, 812® and 818® by the company Dynamit Nobel;

synthetic ethers containing from 10 to 40 carbon atoms, such as dicaprylyl ether;

hydrocarbon-based esters of formula RCOOR' in which RCOO represents a carboxylic acid residue comprising from 2 to 40 carbon atoms, and R' represents a hydrocarbon-based chain containing from 1 to 40 carbon atoms, such as cetostearyl octanoate, isopropyl alcohol esters, such as isopropyl myristate or isopropyl palmitate, ethyl palmitate, 2-ethylhexyl palmitate, isopropyl stearate or isostearate, isostearyl isostearate, octyl stearate, 2-ethylhexylhydroxysterate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate and palmitate, polyethylene glycol diheptanoate, propylene glycol 2-diethyl hexanoate, hexyl laurate, neopentanoic acid esters, for instance isodecyl neopentanoate, isotridecyl neopentanoate, isostearyl neopentanoate and 2-octyldodecyl neopentanoate, isononanoic acid esters, for instance isononyl isononanoate, isotridecyl isononanoate and octyl isononanoate, oleyl erucate, isopropyl lauroyl sarcosinate, diisopropyl sebacate, isocetyl stearate, isodecyl neopentanoate, isostearyl behenate, and myristyl myristate;

fatty alcohols containing from 12 to 26 carbon atoms, for instance octyldodecanol, 2-butyloctanol, 2-hexyldecanol, 2-undecylpentadecanol and oleyl alcohol;

higher $C_{12}$-$C_{22}$ fatty acids, such as oleic acid, linoleic acid and linolenic acid, and mixtures thereof;

fatty acids containing from 12 to 26 carbon atoms, for instance oleic acid;

dialkyl carbonates, the two alkyl chains possibly being identical or different, such as dicaprylyl carbonate sold under the name Cetiol CC® by Cognis; and aromatic esters such as tridecyl trimellitate, $C_{12}$-$C_{15}$ alcohol benzoate, 2-phenylethyl benzoate, and butyloctyl salicylate, hydroxylated esters such as polyglycerol-2 triisostearate, esters of $C_{24}$-$C_{28}$ branched fatty acids or fatty alcohols such as those described in patent application EP-A-0 955 039, and especially triisoarachidyl citrate, pentaerythrityl tetra isononanoate, glyceryl triisostearate, glyceryl tris(2-decyl)tetradecanoate, pentaerythrityl tetraisostearate, polyglyceryl-2 tetraisostearate or pentaerythrityl tetrakis(2-decyl)tetradecanoate, esters and polyesters of dimer diol and of monocarboxylic or dicarboxylic acid, such as esters of dimer diol and of fatty acid and esters of dimer diol and of dimer dicarboxylic acid, such as Lusplan DD-DA5® and Lusplan DD-DA7® sold by the company Nippon Fine Chemical and described in patent application US 2004-175 338, the content of which is incorporated into the present application by reference, and mixtures thereof.

In a preferred embodiment, the oil is selected from 2-ethylhexyl hydroxystearate, (or octyl hydroxystearate), ethylhexyl ethylhexanoate, castor oil, or any combination thereof, and more particularly is 2-ethylhexyl hydroxystearate, (or octyl hydroxystearate).

In a preferred embodiment for the oily dispersion of reflective agent used for making the inner core of the microcapsule, the amount of reflective agent in the dispersion ranges from 50% to 90% by weight, more preferably from 60% to 80% by weight, more particularly from 65% to 75% by weight of the total weight of the dispersion. The amount of the oil is therefore in the range of from 10% to 50% by weight, more preferably from 20% to 40% by weight, more particularly, from 25% to 35% by weight relative to the total weight of the dispersion, respectively.

In a preferred embodiment, the weight ratio of the reflective agent particles to the oil(s) ranges from 1.5/1 to 5/1, more preferably from 1.5/1 to 3/1, particularly from 2/1 to 4/1, and more particularly from 2/1 to 3/1.

According to a particular form of the invention, the oily dispersion dispersion of reflective agent is a dispersion of bismuth oxychloride in ethylhexyl hydroxystearate, more particularly a dispersion containing from 68% to 72% by weight of bismuth oxychloride in 28% to 32% by weight of 2-ethylhexyl hydroxystearate relative to the total weight of the dispersion, Such a dispersion is particularly sold under the commercial name Biron Liquid Silver® or Timiron® Liquid Silver, by the company MERCK.

According to a preferred embodiment of the present invention, the amount of the inner core of the microcapsules constituted by the oily dispersion of reflective agent, is within a range of from 20% to 90% %, by weight., more preferably from 30% to 90% %, by weight, in particular from 40% to 90% by weight, more particularly from 50% to 90% by weight, more better from 60% to 90%, by weight, more advantageously from 70% to 90%%, by weight., more advantageously from 70% to 80%, by weight, more particularly advantageously from 60% to 80%, by weight relative to the total weight of the microcapsule.

In some of any of the embodiments described herein, the microcapsule contains only one type of a reflective agent or a mixture of two or more reflective agents, either encapsulated individually, and/or one or more blends of reflective agents may be encapsulated within the inner core of the microcapsules. A person skilled in the art will know how to choose reflective agent and combinations of reflective agents to produce a desired effect on the skin.

The Wall-Forming Materials a) Wall-Forming polymer

The wall-forming material forms the outer shell(s) of the microcapsules of the present embodiments, and serves as a membrane for the encapsulated substance (the reflective agent). According to embodiments of the present invention, the wall forming material forming the outer shell(s) comprises a wall-forming polymer or co-polymer. In some of any of the embodiments of the present invention, one or more of the outer shells further comprise at least one opaque substance and/or at least one fatty acid salt, and may optionally further comprise at least one plasticizer.

The phrase "wall-forming polymer", which is also referred to herein as "wall-forming polymeric material" refers to a polymeric material (e.g., a polymer or copolymer) or a combination of two or more different polymeric materials, as defined herein, which form a component of the external wall or layer or shell of single-layer microcapsules, or, in the case of multi-layer microcapsules, additionally of the one or more intermediate shells between the inner core and the external (outer most) layer. In the context of single-layer microcapsules, the term "polymer shell" refers to a polymer layer comprised of the wall-forming polymer(s), which envelopes the inner core. In the context of multi-layer microcapsules, the term "polymer shell" refers to any of the polymer layers which envelopes the inner core, or which envelopes the preceding polymer layer.

In some embodiments, the wall-forming polymer is selected so as to sustain shear forces applied while being compounded in industrial processes, but, nevertheless, so as to provide microcapsule which are rupturable when applied (e.g., rubbed or pressed) on the skin.

In some embodiments, the wall-forming polymeric material comprises a polymer containing a sufficient amount of functional groups which are capable of forming hydrogen bonds.

In some embodiments, the polymeric material forming the one or more outer shells independently comprises hydrogen bond-forming functional groups featuring 4-40 weight percents of total polymer weight. Hydrogen bond-forming functional groups include, but are not limited to, functional groups which comprise one or more electron-donating atom(s) such as oxygen, sulfur and/or nitrogen.

In some embodiments, the hydrogen bond-forming groups include carboxylic acid, carboxylate, hydroxy, or any combination thereof.

In some embodiments, one or more, or each, of the wall-forming polymeric materials forming the outer shell(s) comprises a polyacrylate, a polymethacrylate, a cellulose ether or ester, or any combination thereof.

Exemplary wall-forming polymeric materials include, but are not limited to, polyacrylates, polymethacrylates, low molecular weight poly(methyl methacrylate)-co-(meth-acrylic acid) (e.g., 1:0.16), poly(ethyl acrylate)-co-(methyl methacrylate)-co-(trimethylammmonium-ethyl methacrylate chloride) (e.g., 1/2/0.1) (also known as Eudragit® RSPO), poly(butyl methacrylate)-co-(2-dimethylaminoethyl methacrylate)-co-(methyl methacrylate) (e.g., 1/2/1), poly(styrene)-co-(maleic anhydride), copolymer of octylacrylamide, cellulose ethers, cellulose esters, poly(ethylene glycol)-block-poly(propylene glycol)-block-poly(ethylene glycol), PLA (poly(lactic acid), PGA (poly(glycolide), PLGA (poly(lactide)-co-poly(glycolide) or any combination thereof.

Any combination of polymers and co-polymers as described herein is contemplated for a wall-forming material, as described herein.

In some embodiments, the wall-forming polymeric material of an outer shell comprises a cellulose ether or ester such as, but not limited to, methyl cellulose, ethyl cellulose, hydroxypropyl methyl cellulose, hydroxypropyl cellulose, cellulose acetate, cellulose acetate phthalate, cellulose acetate butyrate and hydroxypropyl methyl cellulose acetate phthalate. When a cellulose ether or ester is used in the polymeric material, it preferably contains 4-20% hydroxyl groups which are free to form hydrogen bonds (e.g., hydroxyl groups which are not alkylated or acylated).

In some of any of the embodiments described herein, the wall-forming material of an outer shell comprises an acrylate/ammonium methacrylate copolymer such as, for example, Eudragit® RSPO. In some of any of the other embodiments of the present invention, the wall-forming material of an outer shell comprises a combination of the above-mentioned polymers such as, but not limited to, combinations of acrylate/ammonium methacrylate copolymer (e.g., Eudragit® RSPO) with either poly(methyl methacrylate), poly(methacrylate), poly(methyl methacrylate)-co-(methacrylic acid) or cellulose acetate.

When two polymeric materials are used as a wall-forming material, a weight ratio therebetween can range from 10/1 to 1/1, and can be, for example, 5/1, 4/1, 3/1, 2/1, or 3/2.

In some of any of the embodiments described herein, the wall forming material is or comprises poly(methyl methacrylate (PMMA).

In some of any of the embodiments described herein, the wall forming material is or comprises a poly(methyl methacrylate)-co-(methacrylic acid) (PMMA/MA).

In some of any of the embodiments described herein, the wall forming material is or comprises an acrylate/ammonium methacrylate copolymer (e.g., Eudragit® RSPO). In some of any of the embodiments described herein, the wall forming material is or comprises cellulose acetate.

The amount (weight/weight) of the wall-forming polymer(s) of the outer shell relative to the total microcapsule weight can be within a range of from 5% to 30% by weight, more preferably from about 5% to 20% by weight, particularly from about 5% to about 15% by weight, more particularly from about 5% to about 10% by weight.

In some embodiments, when the wall-forming material is a cellulose ester such as cellulose acetate, and the outer shell may not comprise a fatty acid salt, as described herein. In some such embodiments, the outer shell comprises an opaque substance, such as $TiO_2$, in an amount higher than 10% by weight, for example, in an amount ranging from 20% to 40% by weight, more preferably from 30% to 40% by weight relative to the total weight of the microcapsule.

In embodiments when the wall-forming material is cellulose acetate, the amount of the cellulose acetate can be, for example, from 5% to 10% by weight, more preferably from 5% to 8% by weight, and in particular 5% by weight relative to the total weight of the composition.

In embodiments related to multi-layer microcapsules, the wall-forming material in each of the outer shells in the microcapsules described herein (e.g., a first wall-forming material of the inner core, a second wall-forming material of a first outer shell enveloping the inner core, and optionally a third wall-forming material of a second outer shell enveloping the first outer shell, and so forth) can be the same or different.

b) Opaque Substance:

The outer shell of the single-layer microcapsules described herein can be opaque, semi-opaque or non-opaque (transparent). In some embodiments, the outer shell is opaque, and thus masks the light reflectance imparted by the reflective agent.

In some embodiments, one or more of the outer shells of multi-layer microcapsules as described herein can be opaque, semi-opaque or non-opaque (transparent). In some embodiments, one or more of the outer shells (e.g., the most outer shell) is opaque, and thus masks the light reflectance imparted by the reflective agent.

In some embodiments of the present invention, opacity of the outer shell of the microcapsules is obtained by an inclusion of an opaque substance.

As used herein, an "opaque substance" is a substance which is non-transparent and blocks at least 70% of the light passing therethrough.

Thus, an opaque outer shell blocks 70% to 100% of the light. Semi-opaque outer shell blocks up to 50% of the light. Non-opaque or transparent outer shell blocks no more than 30% of the light passing therethrough.

The terms "opacity" and "opaque" refer to herein to UV-vis light, such as, for example, daylight.

Exemplary opaque substances include, but are not limited to, $TiO_2$, zinc oxide, alumina, boron nitride, talc, mica and any combination thereof.

The total amount of opaque substance(s) in the outer shell is within a range of from 1% to 50% by weight, more preferably from 1% to 40% by weight, more particularly from 10% to 40% by weight, relative to the total weight of the microcapsule.

In some of any of the embodiments described herein, the opaque substance is, or comprises, $TiO_2$, and in some embodiments, an amount of $TiO_2$ is within a range of from 1% to about 30% by weight, preferably from 10% to 40%, by weight, of the total weight of the microcapsule.

In some of any of the embodiments described herein, the opaque substance is, or comprises, $TiO_2$, and in some embodiments, an amount of $TiO_2$ is about 10% by weight relative to the total weight of the microcapsule.

In some of any of the embodiments described herein, the opaque substance is, or comprises, $TiO_2$, and in some embodiments, an amount of $TiO_2$ is about 35% by weight relative to the total weight of the microcapsule.

In some embodiments, the outer shell does not comprise an opaque substance as described herein.

c) Fatty Acid Salt:

In some of any of the embodiments described herein, an outer shell optionally comprises an opaque substance as described herein in any one of the respective embodiments, and/or alternatively, or in addition, further comprises a fatty acid salt as described herein in any one of the respective embodiments.

A fatty acid salt comprises a long hydrophobic hydrocarbon chain (e.g., of 4 to 30 carbon atoms in length) carboxylate anion (a fatty acyl) and a cation, as depicted in the following formula:

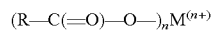

$(R-C(=O)-O-)_n M^{(n+)}$ wherein R is a substituted or unsubstituted, liner or branched hydrocarbon chain of 4 to 30 carbon atoms, $M^+$ is a cation, preferably a metal cation, and n is an integer representing the number of fatty acyls that interact with the cation, and also represents the charge number of the cation (e.g., 1, 2, 3, etc.).

The fatty acid salts that are usable in some of any of the embodiments of the present invention may contain 1 to 3 fatty acyl chains, each chain, independently, comprising 4 to 30 or 8 to 24 carbon atoms (C8-C24) in length. Thus, the fatty acid salt can be a salt of a monovalent, divalent or trivalent metal ion or a salt of an organic cation.

A monovalent metal ion can be, for example, $Na^+$, $K^+$, $Cs^+$, $Li^+$; a divalent metal ion is selected from $Mg^{2+}$, $Ca^{2+}$, Fe (II), Co2+, $Ni^{2+}$, $Cu^{2+}$, $Mn^{2+}$, $Cd^{2+}$, $Sr^{2+}$ or $Zn^{2+}$; a thrivalent metal ion can be, for example, Fe(III), $La^{3+}$, $Eu^{3+}$ or $Gd^{3+}$; an organic cation can be, for example, ammonium, sulfonium, phosphonium or arsonium.

The fatty acyl can be derived from fatty acids such as, but not limited to, stearic acid, arachidic acid, palmitoleic acid, oleic acid, linoleic acid, linolaidic acid, arachidonic acid, myristoleic acid and erucic acid. Other fatty acids are also contemplated. Exemplary fatty acid salts include, but are not limited to, magnesium stearate, magnesium oleate, calcium stearate, calcium linoleate, sodium stearate, magnesium arachidnoate, magnesium palmitate, magnesium linoleate, calcium arachidonoate, calcium myristoleate, sodium linoleate, calcium linoleate, sodium stearate, potassium stearate, sodium laurate, sodium myristate, sodium palmitate, potassium laurate, potassium myristate, potassium palmitate, calcium laurate, calcium myristate, calcium palmitate, zinc laurate, zinc myristate, zinc palmitate, zinc stearate, magnesium laurate, and magnesium myristate.

In a preferred embodiment, the fatty acid salt is magnesium stearate.

The fatty acid salt is usually in an amount within a range of from 0.05% to 5% by weight, more preferably from 0.1% to 4.5% by weight, particularly from 0.2% to 4% by weight, more particularly from 0.5% to 4%, advantageously from 0.5% to 3.0% by weight, more advantageously from 0.75% to 3.0% by weight, particularly more advantageously from 1.0% to 3.0% by weight, more better from 1.0% to 2.0% by weight, and in particular is 1.0%, by weight relative to the total microcapsule's weight.

Without being bound by any particular theory, it is assumed that the cation of the fatty acid salt attracts the particles of an opaque substance and optionally the free carboxylic and/or hydroxyl groups of the wall-forming polymer, resulting in a better adhesion of both the opaque substance and the polymeric material to the inner core, thereby providing efficient masking of the oily dispersion of oxychloride bismuth present in the inner core.

Fatty acid salts may be used in the preparation of single-layer microcapsules while being added to the organic phase together with the encapsulated material, and the wall-forming polymer, with or without the opaque substance. Upon contacting the organic phase with an aqueous phase, the fatty chains will spontaneously wrap around the encapsulated substance and their polar/ionic heads will interact with the oppositely charged opaque substance as well as with oppositely charged groups on the polymer, thereby enhancing the formation of an opaque polymeric envelope surrounding a core comprising the encapsulated material.

d) Plasticizer:

In some embodiments of any of the embodiments of the present invention, an outer shell of the microcapsules further comprises a plasticizer.

Herein and in the art, a "plasticizer" describes a substance which increases the plasticity or fluidity of a composition. In the context of the present embodiments, a plasticizer is added to the wall-forming material in order to control the physical properties and level of elasticity of the microcapsule's outer shells.

Exemplary plasticizers include, but are not limited to, triethyl citrate, tricaprylin, trilaurin, tripalmitin, triacetin, acetyltriethyl citrate, paraffin oil, and any combination thereof. In exemplary embodiments, the plasticizer is triethyl citrate.

The amount of the plasticizer can be within a range of from 0.5% to about 30% by weight, preferably from 0.5% to 20% by weight, more preferably from 1.0% to 20% by weight, particularly from 5% to 15% by weight, more particularly from 5% to 10% by weight, advantageously is 10% by weight relative to the total weight of the microcapsule.

Exemplary Compositions of Microcapsules:

In a most preferred embodiment of the present invention, the microcapsules as described herein comprise, as the inner core, bismuth oxychloride dispersed in 2-ethylhexyl hydroxystearate. In some of these embodiments, the amount of the inner core is at least 50% by weight, more preferably from 60 to 80% by weight (for example, 60%, or 70%, or 79%, or 80%) relative to the total weight of the microcapsule.

In particular, the microcapsules are single-layer microcapsules, and the outer shell comprises magnesium stearate in an amount within a range of from 1.0% to 2.0% by weight, and $TiO_2$ in an amount within a range of from 5% to 15%, by weight relative to the total weight of the microcapsule.

In some of these embodiments, the amount of the wall-forming polymer(s) ranges from 5% to 15% by weight relative to the total weight of the microcapsule.

In some of these embodiments, the wall-forming polymer is selected from a poly (methyl methacrylate) or a copolymer of methyl methacrylic acid and acrylic acid or acrylate/ammonium methacrylate copolymer.

In some exemplary embodiments of the present invention, the microcapsules are single-layer microcapsules, and the outer shell comprises $TiO_2$ in an amount within a range of from 30% to 40%, by weight relative to the total weight of the microcapsule, and does not comprise a fatty acid salt. In some of these embodiments, the wall-forming polymer is a cellulose ester such as cellulose acetate.

In some exemplary embodiments, a microcapsule as described herein is a single-layer microcapsule and comprises a reflective agent as described herein in an amount of about 60-80% by weight, a wall-forming polymer or copolymer in an amount of 5-10% by weight, magnesium stearate in an amount of 0-1% by weight, and $TiO_2$ in an amount of 0-35% by weight relative to the total weight of the microcapsule.

In a preferred embodiment of the invention, the microcapsules are single-layer microcapsules.

In a preferred embodiment of the invention, the microcapsules are single-layer microcapsules comprising the inner core constituted by bismuth oxychloride dispersed in 2-ethylhexyl hydroxystearate in an amount from 60 to 80% by weight, the outer shell comprises magnesium stearate in an amount within a range of from 1.0% to 2.0% by weight, $TiO_2$ in an amount within a range of from 1% to 20% by weight, more preferably from 5% to 15% by weight, more particularly in an amount of 10%, by weight, and, as a wall-forming polymer, PMMA, in an amount within a range of from 5% to 20% by weight, more preferably in an amount of 10%, by weight, relative to the total weight of the microcapsule. An exemplary such composition is presented in Example 1 hereinafter. The amount of the raw material (oily dispersion of bismuth oxychloride) used to prepare the microcapsules is 79% by weight of the total weight of the microcapsule.

In another preferred embodiment of the invention, the microcapsules are single-layer microcapsules comprising the inner core constituted by bismuth oxychloride dispersed in 2-ethylhexyl hydroxystearate in an amount of from 60 to 80% by weight, the outer shell does not comprise magnesium stearate, and comprises $TiO_2$ in an amount within a range of 10% to 50% by weight, more preferably from 10% to 40%, more particularly from 20% to 40% by weight, advantageously from 30% to 40% by weight more advantageously in an amount of 25% by weight, and, as a wall-forming polymer, ethyl cellulose, in an amount within a range of 1% to 10% by weight, more preferably in an amount of 5%, by weight relative the total weight of the microcapsule. An exemplary such composition is presented in Example 2 hereinafter. The amount of the raw material (oily dispersion of reflective agent) used to prepare the microcapsules is 60% by weight of the total weight of the microcapsule.

In another preferred embodiment of the invention, the microcapsules are single-layer microcapsules comprising the inner core constituted by bismuth oxychloride dispersed in 2-ethylhexyl hydroxystearate in an amount of from 60 to 80% by weight, and the outer shell comprises magnesium stearate in an amount within a range of from 1.0% to 2.0%, by weight, $TiO_2$ in an amount within a range of 1% to 20% by weight, preferably from 5% to 15% by weight, more preferably in an amount of 10% by weight, and, as a wall-forming polymer EUDRAGIT® RS PO (Poly(ethyl acrylate-co-methyl methacrylate-co-trimethyl ammonium ethyl methacrylate chloride), in an amount within a range of 5% to 20% by weight, more preferably in an amount of 10%, by weight relative the total weight of the microcapsule. An exemplary such composition is presented in Example 3 hereinafter. The amount of the raw material (oily dispersion of bismuth oxychloride) used to prepare the microcapsules is 79% by weight relative to the total weight of the microcapsule.

In another preferred embodiment of the invention, the microcapsules are single-layer microcapsules.comprising the inner core constituted by bismuth oxychloride dispersed in 2-ethylhexyl hydroxystearate in an amount of from 60 to 80% by weight, the outer shell comprises magnesium stearate in an amount within a range of from 1.0% to 2.0% by weight, $TiO_2$ in an amount within a range of 1% to 20% by weight, more preferably from 5% to 15% by weight, more particularly in an amount of 10% by weight, and, as a wall-forming polymer, PMMA/MA, in an amount within a range of 5% to 20% by weight, more preferably in an amount of 10% by weight relative to the total weight of the microcapsule. An exemplary such composition is presented in Example 4 hereinafter. The amount of the raw material (oily dispersion of bismuth oxychloride) used to prepare the microcapsules is 79% by weight of the total weight of the microcapsule.

In another preferred embodiment of the invention, the microcapsules are single-layer microcapsules comprising the inner core constituted by bismuth oxychloride dispersed in 2-ethylhexyl hydroxystearate in an amount of from 60 to 80% by weight, the outer shell does not comprise magnesium stearate nor $TiO_2$, and comprises a plasticizer, in an amount within a range of 1% to 20% by weight, preferably from 5% to 15% by weight, more preferably, in an amount of 10% by weight, and, as a wall-forming material, EUDRAGIT® RS PO (Poly(ethyl acrylate-co-methyl methacrylate-co-trimethyl ammonium ethyl methacrylate chloride), in an amount within a range of 5% to 20% by weight, more preferably in an amount of 10% by weight relative to the total weight of the microcapsule. An exemplary such composition is presented in Example 5 hereinafter. The amount of the raw material (oily dispersion of bismuth oxychloride) used to prepare the microcapsules is 80% by weight of the total weight of the microcapsule.

The Process for the Preparation of the Microcapsules:

The process used for the preparation of the microcapsules according to embodiments of the present invention is a modification of the microencapsulation solvent removal method disclosed, for example, in U.S. Pat. Nos. 6,932,984 and 7,838,037 and WO 2012/156965, which are incorporated by reference as if fully set forth herein. According to this technology, the active ingredient is found in the core of the microcapsule. This technique seals each micro-capped ingredient from chemical and cross-link reactions, degradation, color change or loss of potency during production, and for extended periods in storage.

The solvent removal process is based on four main steps as follows:

(i) preparing a homogeneous organic solution comprising the encapsulated oily dispersion of reflective agent, and a wall-forming polymeric material, and optionally an opaque substance and/or a fatty acid salt, and an organic solvent that is partially miscible in water;

(ii) preparing an emulsion of an aqueous continuous phase containing an emulsifier and saturated with the same organic solvent of the organic solution, and optionally comprising the opaque substance;

(iii) mixing the homogeneous organic solution with the aqueous emulsion, under high shear stirring to thereby form an emulsion; and (iv) extracting the organic solvent by adding to the emulsion formed in step (iii) an amount of water which initiates extraction of the organic solvent from the emulsion, thereby obtaining the microcapsules.

For multi-layer (e.g., double-layer and triple-layer) microcapsules, the microcapsules are formed by first modifying the surface of the single-layer microcapsules formed according to steps (i)-(iv) and then subjecting the surface-modified inner core microcapsules to one or more cycles of steps (i)-(iv), when the inner core microcapsules are dispersed in the organic solution together with the wall-forming material.

In some embodiments, the microcapsules according to the present embodiments can be prepared a modified solvent removal method comprising the following steps:

(a) contacting an organic phase comprising an oily dispersion of reflective agent, and a wall-forming polymer or copolymer, optionally a fatty acid salt, and optionally an opaque substance and/or a plasticizer, and a first partially water-miscible organic solvent, with an aqueous solution saturated with said organic solvent and comprising an emulsifier, to thereby obtain an emulsion; and (b) adding to the formed emulsion an amount of water which initiates extraction of the organic solvent from the emulsion, thereby obtaining the microcapsules.

In further steps, the microcapsules are isolated following step (b), dried and sifted to thereby obtain a free flowing powder of the microcapsules.

These steps are further detailed as follows:

The homogenous solution prepared in step (a) is obtained by preparing an organic solution or dispersion of a wall-forming polymeric material as described in any one of the respective embodiments described herein, in an organic solvent that is partially miscible in water and is capable of dissolving or dispersing the wall-forming polymer. In exemplary embodiments, the organic solvent is an organic solvent approved for topical applications, such as, but not limited to, ethyl acetate, ethanol, ethyl formate, or any combination thereof. In some embodiments, the organic solvent is ethyl acetate.

The fatty acid salt is as described in any one of the respective embodiments described herein. The opaque substance is as described in any one of the respective embodiments described herein. In preferred embodiments, the opaque substance is $TiO_2$.

When a plasticizer is used, it is usually selected from tricaprylin, trilaurin, tripalmitin, triacetin, triethyl citrate, acetyltriethyl citrate, paraffin oil, or any combination thereof. The components of the organic solution are mixed/stirred until a homogeneous, optionally transparent, solution or dispersion is obtained.

The aqueous continuous phase is saturated with the organic solvent that forms the organic solution, and typically comprises an emulsifier, and optionally the opaque substance (if included in the microcapsule and not included in the organic phase).

The organic solution or dispersion and the aqueous continuous phase are mixed under low sheer stirring to thereby form an emulsion.

In step (b), an amount of water is added to the emulsion prepared in (a), thereby extracting the organic solvent and allowing the r microcapsules to form.

In the context of embodiments of the invention, the term "low sheer stirring" refers to a mixing at about 100-800 rpm, preferably at about 300-600 rpm.

In some embodiments, when the microcapsules are multi-layer microcapsules, the process further comprises: (c) optionally repeating steps (a) and (b), using a second, third, and so on, organic phases and aqueous continuous phases, thereby obtaining multi-layered microcapsules.

Cosmetic Compositions

The compositions according to the invention, are preferably aqueous dispersions wherein the microcapsules are dispersed in the aqueous phase. They may be in the form of aqueous or hydro-alcoholic lotions or serums.

Aqueous Phase

The aqueous phase of a composition according to the invention comprises water and optionally a water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the composition of the invention may also be volatile.

Among the water-soluble solvents that may be used in the composition in accordance with the invention, mention may be made especially of lower monoalcohols containing from 2 to 8 carbon atoms, such as ethanol and isopropanol, glycols containing from 2 to 8 carbon atoms, such as ethylene glycol, propylene glycol, 1,3-butylene glycol and dipropylene glycol, C3 and C4 ketones and C2-C4 aldehydes.

The aqueous phase (water and optionally the water-miscible solvent) may be present in the composition in a content ranging from 20% to 95%, better still from 30% to 80% by weight by weight relative to the total weight of the said composition.

According to another embodiment variant, the aqueous phase of a composition according to the invention may comprise at least one C2-C32 polyol.

For the purposes of the present invention, the term "polyol" should be understood as meaning any organic molecule comprising at least two free hydroxyl groups.

Preferably, a polyol in accordance with the present invention is present in liquid form at room temperature.

A polyol that is suitable for use in the invention may be a compound of linear, branched or cyclic, saturated or unsaturated alkyl type, bearing on the alkyl chain at least two —OH functions, in particular at least three —OH functions and more particularly at least four —OH functions.

The polyols advantageously suitable for the formulation of a composition according to the present invention are those exhibiting in particular from 2 to 32 carbon atoms and preferably from 3 to 16 carbon atoms.

Advantageously, the polyol may be chosen, for example, from ethylene glycol, pentaerythritol, trimethylolpropane, propylene glycol, 1,3-propanediol, butylene glycol, isoprene glycol, pentylene glycol, hexylene glycol, glycerol, polyglycerols such as glycerol oligomers, for instance diglycerol, and polyethylene glycols, and mixtures thereof.

According to a preferred embodiment of the invention, the said polyol is chosen from ethylene glycol, pentaerythritol, trimethylolpropane, propylene glycol, glycerol, polyglycerols and polyethylene glycols, and mixtures thereof.

According to a particular embodiment, the composition of the invention may comprise at least propylene glycol.

According to another particular embodiment, the composition of the invention may comprise at least glycerol.

A water suitable for the invention can be a floral water such as cornflower water and/or a mineral water such as water from Vittel, water from Lucas or water from La Roche Posay, and/or thermal water.

Compositions with Alcohol

According to a particular form of the invention, the composition contains at least one mono-alcohol comprising from 2 to 8 carbon atoms.

According to a particular form of the invention, the composition contains from 0.5% to 10%, and preferably from 1 to 5 by weight relative to the total weight of at least one mono-alcohol comprising from 2 to 8 carbon atoms.

The compositions of the invention comprise at least one mono-alcohol having from 2 to 8 carbon atoms, especially from 2 to 6 carbon atoms, and particularly 2 to 4 carbon atoms.

The compositions of the invention may include one or more mono-alcohol(s).

The monoalcohol may be represented for example by formula RaOH, wherein Ra is an alkyl group, linear or branched, comprising 2 to 8 carbon atoms.

As a monohydric alcohol include ethanol, isopropanol, propanol or butanol.

According to one embodiment, the compositions of the invention include ethanol.

Additives

The compositions according to the invention can also contain additional cosmetic ingredients classically used for the formulation of particular galenic forms, generally adapted to the aimed keratinous material. Those additional cosmetic ingredients can be notably chosen film-forming polymers, non-ionic, anionic and cationic surfactants, hydrophilic or lipophilic gellants or thickeners, dispersants, actives, sunscreen agents, preservatives, antioxidants, solvents, perfumes, fillers other than the particles of the invention, bactericides, odour absorbers, coloring agents (pigments, nacres, water-soluble dyestuffs), salts, and their mixtures.

Coloring Agents

According to a particular mode of the invention, the composition contain at least one particulate or non-particulate, water-soluble or water-insoluble coloring agent preferably in a proportion of at least 0.01% by weight relative to the total weight of the composition.

For obvious reasons, this amount is liable to vary significantly with regard to the intensity of the desired colour effect and of the colour intensity afforded by the coloring agents under consideration, and its adjustment clearly falls within the competence of a person skilled in the art.

For the purposes of the invention, the term "water-soluble coloring agent" means any natural or synthetic, generally organic compound, which is soluble in an aqueous phase or in water-miscible solvents, and which is capable of imparting colour.

As water-soluble dyes that are suitable for use in the invention, mention may be made especially of synthetic or natural water-soluble dyes, for instance FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanin (beetroot), carmine, copper chlorophylline, methylene blue, anthocyanins (enocianin, black carrot, hibiscus and elder), caramel and riboflavin.

The water-soluble dyes are, for example, beetroot juice and caramel.

The particulate coloring agents may especially be pigments, nacres and/or particles with metallic tints.

The term "pigments" should be understood as meaning white or coloured, mineral or organic particles that are insoluble in an aqueous solution, which are intended to colour and/or opacify the composition containing them.

The pigments may be white or coloured, and mineral and/or organic.

As mineral pigments that may be used in the invention, mention may be made of titanium oxide, titanium dioxide, zirconium oxide, zirconium dioxide, cerium oxide or cerium dioxide and also zinc oxide, iron oxide or chromium oxide, ferric blue, manganese violet, ultramarine blue and chromium hydrate, and mixtures thereof. It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

They may also be pigments having a structure that may be, for example, of silica microsphere type containing iron oxide. An example of a pigment having this structure is the product sold by the company Miyoshi under the reference PC Ball PC-LL-100 P, this pigment being constituted of silica microspheres containing yellow iron oxide.

Advantageously, the pigments in accordance with the invention are iron oxides and/or titanium dioxides.

The term "nacres" should be understood as meaning iridescent or non-iridescent coloured particles of any shape, especially produced by certain molluscs in their shell or alternatively synthesized, which have a colour effect via optical interference.

A composition according to the invention may comprise from 0% to 15% by weight of nacres relative to the total weight of the said composition.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres

Timica, Flamenco and Duochrome (based on mica) sold by the company Engelhard, the Timiron nacres sold by the company Merck, the Prestige mica-based nacres sold by the company Eckart, and the Sunshine synthetic mica-based nacres sold by the company Sun Chemical.

The nacres may more particularly have a yellow, pink, red, bronze, orangey, brown, gold and/or coppery colour or tint.

Advantageously, the nacres in accordance with the invention are micas coated with titanium dioxide or with iron oxide, and also bismuth oxychloride.

For the purposes of the present invention, the term "particles with a metallic tint" means any compound whose nature, size, structure and surface finish allow it to reflect the incident light, especially in a non-iridescent manner.

The particles with a metallic tint that may be used in the invention are in particular chosen from:
 particles of at least one metal and/or of at least one metal derivative;
 particles comprising a single-material or multi-material organic or mineral substrate, at least partially coated with at least one layer with a metallic tint comprising at least one metal and/or at least one metal derivative; and
 mixtures of the said particles.

Among the metals that may be present in the said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr, and mixtures or alloys thereof (for example bronzes and brasses) are preferred metals. The term "metal derivatives" denotes compounds derived from metals, especially oxides, fluorides, chlorides and sulfides.

Illustrations of these particles that may be mentioned include aluminum particles, such as those sold under the names Starbrite 1200 EAC® by the company Siberline and Metalure® by the company Eckart and glass particles coated with a metallic layer, especially those described in documents JP-A-09188830, JP-A-10158450, JP-A-10158541, JP-A-07258460 and JP-A-05017710.

Hydrophobic Treatment of the Coloring Agent

The pulverulent dyestuffs as described previously may be totally or partially surface-treated, with a hydrophobic agent, to make them more compatible with the oily phase of the composition of the invention, especially so that they have good wettability with oils. Thus, these treated pigments are well dispersed in the oily phase. Hydrophobic-treated pigments are described especially in document EP-A-1 086 683.

The hydrophobic-treatment agent may be chosen from silicones such as methicones, dimethicones and perfluoroalkylsilanes; fatty acids, for instance stearic acid; metal soaps, for instance aluminium dimyristate, the aluminium salt of hydrogenated tallow glutamate; perfluoroalkyl phosphates; polyhexafluoropropylene oxides; perfluoropolyethers; amino acids; N-acylamino acids or salts thereof; lecithin, isopropyl triisostearyl titanate, isostearyl sebacate, and mixtures thereof.

The term "alkyl" mentioned in the compounds cited above especially denotes an alkyl group containing from 1 to 30 carbon atoms and preferably containing from 5 to 16 carbon atoms.

The amount of coloring agent (s) can range, for example, from 0.05 to 10% by weight and better still from 0.1 to 8% by weight, with respect to the total weight of the composition.

Fillers

According to a particular mode of the invention, the composition contain at least one filler.

WO 2017/036538 PCT/EP2015/070174

For the purposes of the present invention, the term "fillers" should be understood as meaning colourless or white solid particles of any form, which are in an insoluble and dispersed form in the medium of the composition.

These fillers, of mineral or organic, natural or synthetic nature, give the composition containing them softness and give the makeup result a matt effect and uniformity.

The fillers in the composition according to the present invention may be in lamellar form (or platelet), spherical (or globular), fiber or any other intermediate form between these defined forms.

Spherical Charges

Spherical fillers used according to the invention have the shape or substantially the shape of a sphere and may be hollow or solid. Advantageously, the spherical fillers of the invention have a particle size (number average diameter) of from 0.1 .mu.m to 250 µm, preferably from 1 µm to 150 µm, more preferably from 10 to100 µm.

The spherical fillers may be organic or mineral microspheres. As organic spherical fillers include for example polyamide powders and especially Nylon® powders such as Nylon-12 or Polyamide 12, sold under the names ORGASOL by Arkema; polyethylene powders; polytetrafluoroethylene powders (Teflon*); microspheres based on acrylic copolymers, such as copolymer of ethylene glycol dimethacrylate/lauryl methacrylate copolymer sold by Dow Corning under the name Polytrap; expanded powders such as hollow microspheres and especially the microspheres sold under the name Expancel by Kemanord Plast or under the name Micropearl F 80 ED by Matsumoto; silicone resin microbeads such as those sold under the name Tospearl by Toshiba Silicone; polymethyl methacrylate microspheres, sold under the name Microsphere M-100 by Matsumoto or under the name Covabead LH85 by Wacker; ethylene acrylate copolymer powders, such as those sold under the name Flobeads by Sumitomo Seika Chemicals; powders of natural organic materials such as starch powders, especially of corn starch, wheat or rice, crosslinked or otherwise, such as the powders of starch crosslinked with octenyl succinate anhydride, sold under the name Dry-FLO by National Starch; metal soaps derived from organic carboxylic acids having 8 to 22 carbon atoms, preferably from 12 to 18 carbon atoms, for example, zinc stearate, magnesium or lithium, zinc laurate, myristate magnesium, Polyporus the L*200 (Chemdal Corporation), polyurethane powders, in particular, powders of crosslinked polyurethane comprising a copolymer, said copolymer comprising trimethylol hexyl lactone as the polymer of hexamethylene diisocyanate/trimethylol hexyl lactone, sold under the name Plastic Powder D-400® or Plastic Powder D-800® by the company Toshiki, carnauba microwaxes, such as that sold under the name MicroCare 350® by the company Micro Powders, microwaxes of synthetic wax such as that sold under the name MicroEase 114S® by the company Micro Powders, microwaxes consisting of a mixture of carnauba wax and polyethylene wax, such as those sold under the names Micro Care 300® and 310® by the company Micro Powders, microwaxes consisting of a mixture of carnauba wax and of synthetic wax, such as that sold under the name Micro Care 325® by the company Micro Powders, polyethylene microwaxes such as those sold under the names Micropoly 200®, 220®, and 220L® 250S® by the company Micro Powders. As spherical inorganic filler, there may be mentioned the hydrophobic aerogel silica particles.

The hydrophobic silica aerogel particles, advantageously, present a specific surface area per unit mass (MS) of from 200 to 1500 $m^2/g$, preferably from 600 to 1200 $m^2/g$ and better still from 600 to 800 $m^2/g$. The surface area per unit mass can be determined by the nitrogen absorption method called BET (Brunauer—Emmet—Teller) method described in "The Journal of the American Chemical Society", Vol. 60, page 309, February 1938 and corresponding to the international standard ISO 5794/1 (Appendix D). The BET surface area is the total surface area of the said silica aerogel particles.

The hydrophobic silica aerogel particles, preferably have a size, expressed as mean diameter (D [0,5]) and measured according to the method previously described, less than 1500 microns and preferably from 1 to 30 μm, preferably from 5 to 25 μm, preferably 5 to 20 μm and more preferably 5 to 15 μm.

The hydrophobic silica aerogel particles may advantageously have a packed density ρ of 0.04 to 0.10 $g/cm^3$, preferably 0.05 to 0.08 $g/cm^3$.

In the context of the present invention, the packed density ρ can be assessed using the following protocol, said protocol of the packed density:

40 g of powder is poured into a measuring cylinder and then the test piece is placed on a device 2003 in STAV STAMPF Volumeter. The specimen is then subjected to a series of 2500 settlements (this operation is repeated until the difference in volume between two successive tests is less than 2%); then the final volume Vf of packed powder is measured directly on the specimen. The packed density is determined by the mass ratio (m)/Vf, namely 40/Vf (Vf being expressed in $cm^3$ and mg).

According to one embodiment, the hydrophobic silica aerogel particles have a specific surface area per unit volume SV of 5 to 60 $m^2/cm^3$, preferably 10 to 50 $m^2/cm^3$ and more preferably from 15 to 40 m2/cm3. The specific surface area per unit volume is given by the equation: $SV=\rho*SM$ where ρ is the packed density in $g/cm^3$ and SM is the surface area per unit mass expressed in $m^2/g$, as defined above.

The hydrophobic silica aerogel particles are preferably silylated silica aerogel particles (INCI name: SILICA SILYLATE), especially particles of hydrophobic silica aerogels surface modified by trimethylsilyl groups (trimethylsiloxylated silica).

According to a preferred embodiment, the hydrophobic silica aerogel particles can be chosen (s) from:

Aerogel marketed under the trademark VM-2260 (INCI name Silica silylate), by Dow Corning, whose particles have an average size of about 1000 microns and a surface area per unit mass of from 600 to 800 $m^2/g$;

Aerogels marketed by the company Cabot Aerogel TLD under the references 201, 201 and EMT Aerogel, Aerogel TLD 203, Enova Aerogel MT 1100, Aerogel Enova MT 1200.

In a preferred embodiment, the hydrophobic silica aerogel particles will be selected from Aerogel marketed under the trademark VM-2270 (INCI name Silica silylate), by Dow Corning, whose particles have a mean size ranging from 5-15 microns and a surface area per unit mass of from 600 to 800 $m^2/g$.

As spherical inorganic filler, there may also be mentioned as silicas Sunsil 130 sold by Sunjin Chemical (INCI name: SILICA) AND (POLY) METAL OXIDES such as (poly) bismuth oxides.

Lamellar Charges

As indicated above, the platy fillers are fillers of parallelepipedal shape (rectangular or square surface), discoidal (circular surface) or ellipsoidal (oval area), characterized by three dimensions: length, width and height. When the shape is circular, the length and width are identical and correspond to the diameter of a disc, while the height corresponds to the thickness of the disc. When the surface is oval, the length and width respectively correspond to the major axis and the minor axis of an ellipse and the height corresponds to the thickness of the elliptical disc formed by the wafer. When it is a parallelepiped, the length and width can be of identical or different dimensions when they are of the same size, the shape of the surface of the parallelepiped is square; otherwise, the shape is rectangular. As for the height, it is the thickness of the parallelepiped.

The lamellar fillers used according to the invention have a length ranging from 0.01 to 100 μm, preferably from 0.1 to 50 microns and preferably from 1 to 50 μm. Platelets have a width ranging from 0.01 to 100 μm, preferably from 0.1 to 50 μm and preferably 1 to 10 μm. Platelets have a height (thickness) of from 0.1 nm to 1 micron, preferably 1 to 600 nm and preferably from 1 to 500 nm.

As lamellar fillers used in the composition of the invention include phyllosilicates, such as talcs, micas, perlite and mixtures thereof.

Talcs are hydrous magnesium silicates comprising mostly aluminum silicate. The crystalline structure of talc consists in repeated layers of a brucite sandwich between the layers of silica. As talc, there may be mentioned the product sold under the name Micro Ace P3 by Nippon Talc (INCI name: talc), that sold under the name Luzenac 00 Imerys (INCI name: TALC), or the product sold under the name Luzenac Pharma M by Imerys (INCI name: TALC).

The micas are aluminum silicates optionally comprising iron and/or alkali metals. They have the property that it can be divided into thin layers (about 1 micron). They usually have a size of from 5 to 150 μm, preferably from 10 to 100 μm and more preferably from 10 to 60 μm for the largest dimension (length) and a height (thickness) of 0.1 to 0.5 μm. Among the micas, it may be mentioned phlogopite, muscovite, fluorophlogopite, vermiculite, and mixtures thereof. As mica, there may be mentioned the product sold under the name S-sericite-152 BC by Miyoshi Kasei (INCI name: mica), Mearlmica Treated SVA sold by BASF Personal Care Ingredients (INCI name: MICA (AND) LAUROYL LYSINE).

Among the phyllosilicates, mention may also be perlite and preferably the perlite.

The perlite used according to the invention are generally aluminosilicate volcanic origin and composition as:
70.0 to 75.0% by weight of silica $SiO_2$
12.0 to 15.0% by weight of aluminum oxide $Al_2O_3$ oxide
3.0-5.0% sodium oxide $Na_2O$
3.0-5.0% of potassium oxide $K_2O$-0.5-2% of iron oxide $Fe_2O_3$
0.2-0.7% of magnesium oxide MgO
0.5-1.5% calcium oxide CaO
0.05 to 0.15% titanium oxide $TiO_2$ Perlite is milled, dried and then calibrated in a first step. The product obtained is said Perlite Ore gray in color and size of the order of 100 microns. Perlite Ore is then expanded (1000° C./2 seconds) to give particles more or less white. When the temperature reaches 850-900° C., the water trapped in the structure of the material vaporizes and causes the material to expand over its original volume. The expanded perlite particles according to the invention can be obtained by the expansion process described in U.S. Pat. No. 5,002,698.

Preferably the perlite particles used will be crushed; in this case they are called Expanded Perlite Milled (EMP). They preferably have a particle size defined by a median diameter D50 of from 0.5 to 50 microns and preferably from 0.5 to 40 µm.

Preferably the perlite particles used have a bulk density loose packed at 25° C. ranging from 10 to 400 kg/m³ (DIN 53468) and preferably 10 to 300 kg/m³.

Preferably, it will be used expansed perlite particles sold under the trade names OPTIMAT 1430 OR or OPTIMAT 2550 by the company WORLD MINERALS.

May be mentioned also nitride boron, sericite, barium sulfate ($BaSO_4$), alumina ($Al_2O_3$) particles.

According to a preferred embodiment of the present invention, the (the) lamellar fillers (s) is (are) chosen (s) from talcs, micas, perlite, boron nitride and mixtures thereof.

In a preferred embodiment, the filler(s) is (are) selected from polyamide powders, elastomeric organopolysiloxane powders, metal soaps, silicas, (poly) metal oxides, hydrophobic silica aerogel particles, perlite, talcs, micas, boron nitride and a mixture thereof, preferably a mixture thereof.

In a preferred embodiment, the fillers are selected from OPTIMAT 1430 OR or OPTIMAT 2550 by the company WORLD MINERALS sold by Word Minerals, VM-2270 Aerogel Fine Particles sold by Dow Corning (INCI name: SILICA SILYLATE); Micro Ace P3 sold by Nippon Talc (INCI name: TALC); Sunsil 130 sold by Sunjin Chemical (INCI name: silica); Luzenac 00 sold by Imerys (INCI name: TALC); Orgasol 2002 sold by Arkema (INCI name: Nylon-12); Boron Nitride ays sold under the trade name SOFTOUCH BORON NITRIDE POWDER CC6058 by Momentive Performance Materials, magnesium stearate sold by Stearinerie Dubois; sericite S-152-BC sold by Miyoshi Kasei (INCI name: MICA); and mixtures thereof, preferably mixtures thereof.

The amount of filler(s) can range, for example, from 0.05 to 10% by weight and better still from 0.1 to 5% by weight, with respect to the total weight of the composition.

Non-Emulsifying Organopolysiloxane Elastomer

According to a particular mode of the invention, the composition contains at least one non-emulsifying organopolysiloxane elastomer.

The organopolysiloxane elastomer, usable as a lipophilic gelling agent, has the advantage of giving the composition according to the invention good application properties. It provides a very soft matting and after application, particularly advantageous for application to the skin. It may also allow effective hiding of pores present on the keratin materials. The compositions of the invention have a good wearing of the pores masking.

By "organopolysiloxane elastomer" or "silicone elastomer" refers to a flexible organopolysiloxane deformable having viscoelastic properties, and especially the consistency of a sponge or of a flexible sphere. Its modulus of elasticity is such that this material is resistant to deformation and has a limited capacity for expansion and contraction. This material is capable of regaining its original shape after stretching.

This is particularly a crosslinked organopolysiloxane elastomer.

Thus, the organopolysiloxane elastomer can be obtained by addition reaction of diorganopolysiloxane containing at least one hydrogen linked to silicon and of diorganopolysiloxane containing ethylenically unsaturated groups linked to silicon, especially in the presence of a platinum catalyst; or by dehydrogenation crosslinking condensation reaction between a hydroxyl terminated diorganopolysiloxane and a diorganopolysiloxane containing at least one hydrogen bonded to silicon, particularly in the presence of an organotin compound; or by crosslinking condensation reaction of a diorganopolysiloxane with hydroxyl end groups and of a hydrolysable organopolysilane; or by thermal crosslinking of organopolysiloxane, especially in the presence of an organoperoxide catalyst; or by crosslinking of organopolysiloxane by high-energy radiation such as gamma rays, ultraviolet rays or an electron beam. Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon especially in the presence (C) platinum catalyst, as described for example in EP-A-295886.

In particular, the organopolysiloxane elastomer can be obtained by reaction of dimethylpolysiloxane containing dimethylvinylsiloxy end groups and of a methylhydropolysiloxane comprising trimethylsiloxy endings in the presence of a platinum catalyst.

The compound (A) is the base reagent for the formation of elastomeric organopolysiloxane and the crosslinking is carried out by an addition reaction of compound (A) with the compound (B) in the presence of catalyst (C).

The compound (A) is an organopolysiloxane having at least two hydrogen atoms bonded to different silicon atoms in each molecule.

The compound (A) may have any molecular structure, in particular a straight chain or branched chain structure or a cyclic structure. The compound (A) may have a viscosity at 25° C. ranging from 1 to 50,000 centistokes, especially have good miscibility with compound (B). The organic groups bonded to silicon atoms of the compound (A) may be alkyl groups such as methyl, ethyl, propyl, butyl, octyl; substituted alkyl groups such as 2-phenylethyl, 2-phenylpropyl, 3,3,3-trifluoropropyl; aryl groups such as phenyl, tolyl, xylyl; substituted aryl groups such as phenylethyl; and substituted monovalent hydrocarbon groups such as an epoxy group, a carboxylate ester group or a mercapto group.

Compound (A) can be selected from trimethylsiloxy-terminated methylhydrogenpolysiloxanes, copolymers terminated dimethylsiloxane-methylhydrogensiloxane containing trimethylsiloxy, cyclic dimethylsiloxane-methylhydrogensiloxane copolymers.

The compound (B) is preferably a diorganopolysiloxane having at least two lower alkenyl groups (e.g. C2-C4); the lower alkenyl group may be selected from vinyl, allyl, and propenyl. These lower alkenyl groups can be located in any position of the organopolysiloxane molecule but are preferably located at the ends of the organopolysiloxane molecule. The organopolysiloxane (B) may have a branched chain structure, a linear, cyclic or network structure but the linear chain structure is preferred. The compound (B) may have a viscosity ranging from the liquid state to the gum state. Preferably, compound (B) has a viscosity of at least 100 centistokes at 25° C.

In addition to the aforementioned alkenyl groups, other organic groups bonded to silicon atoms in the compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon groups such as an epoxy group, a carboxylate ester group or a mercapto group.

The organopolysiloxane (B) can be chosen from methylvinylpolysiloxanes, methylvinylsiloxane-dimethylsiloxane copolymers them, dimethylpolysiloxanes comprising dimethylvinylsiloxy endings, dimethylsiloxane-methylphenylsiloxane copolymers containing dimethylvinylsiloxy end groups, copolymers terminated dimethylsiloxane-diphenylsiloxane-methylvinylsiloxane dimethylsiloxane copolymers, dimethylsiloxane-methylvinylsiloxane trimethylsiloxy end groups, dimethylsiloxane-methylphenylsiloxane-methylvinylsiloxane containing trimethylsiloxy end groups, methyl (3,3,3-trifluoropropyl)-polysiloxane dimethylvinylsiloxy endings and dimethylsiloxane-methyl (3,3,3-trifluoropropyl) siloxane-terminated dimethylpolysiloxane.

In particular, the organopolysiloxane elastomer can be obtained by reaction of dimethylpolysiloxane containing dimethylvinylsiloxy end groups and of methylhydrogen polysiloxane containing trimethylsiloxy end groups, in the presence of a platinum catalyst.

Advantageously, the sum of the number of ethylenic groups per molecule of the compound (B) and the number of hydrogen atoms bonded to silicon atoms per molecule of the compound (A) is at least 5.

It is advantageous that the compound (A) is added in an amount such that the molar ratio between the total amount of hydrogen atoms bonded to silicon atoms in the compound (A) and the total amount of all such groups ethylenically unsaturated compound (B) is in the range of 1.5/1 to 20/1.

The compound (C) is a catalyst for the crosslinking reaction, and is especially chloroplatinic acid, chloroplatinic acid-olefin complexes, chloroplatinic acid-alkenylsiloxane complexes, chloroplatinic acid-diketone, platinum black, and platinum on support.

The catalyst (C) is preferably added from 0.1 to 1000 parts by weight, more preferably from 1 to 100 parts by weight, as clean platinum metal per 1000 parts by weight of the total amount of compounds (A) and (B). The elastomer is preferably a non-emulsifying elastomer.

The term "non-emulsifying" defines organopolysiloxane elastomers not containing a hydrophilic chain, in particular containing no polyoxyalkylene units (in particular polyoxyethylene or polyoxypropylene) or polyglyceryl unit. Thus, in one particular embodiment of the invention, the composition comprises an elastomeric organopolysiloxane devoid of polyoxyalkylene units and polyglyceryl pattern.

In particular, the silicone elastomer used in the present invention is selected from Dimethicone Crosspolymer (INCIname), Vinyl Dimethicone Crosspolymer (INCI name), Dimethicone/Vinyl Dimethicone Crosspolymer (INCI name), Dimethicone Crosspolymer-3 (INCI name).

Organopolysiloxane elastomer particles can be conveyed in the form of a gel consisting of an elastomeric organopolysiloxane included in at least one hydrocarbon oil and/or a silicone oil. In these gels, the organopolysiloxane particles are often non-spherical particles.

Non-emulsifying elastomers are described in patents EP 242 219, EP 285 886, EP 765 656 and in JP-A-61-194009. The silicone elastomer is generally in the form of a gel, a paste or a powder but preferably as a gel in which the silicone elastomer is dispersed in a linear silicone oil (dimethicone) or cyclic (eg cyclopentasiloxane), preferably in a linear silicone oil.

As non-emulsifying elastomers that may be used more particularly those sold under the names "KSG-6", "KSG-15", "KSG-16", "KSG-18", "KSG-41", "KSG-42" "KSG-43", "KSG-44" by the company Shin Etsu, "DC9040", "DC9041" by Dow Corning, "SFE 839" by the company General Electric.

In one particular embodiment, one uses a silicone elastomer gel dispersed in a silicone oil selected from a non-exhaustive list including cyclopentadimethylsiloxane, dimethicones, the dimethylsiloxane the methyl trimethicone, phenylmethicone, phenyldimethicone, phenyltrimethicone and cyclomethicone, of preferably a linear silicone oil selected from the polydimethylsiloxanes (PDMS) or viscosity dimethicones at 25° C. ranging from 1 to 500 cSt at 25° C., optionally modified by aliphatic groups, optionally fluorinated, or with functional groups such as groups hydroxyl, thiol and/or amine.

These include in particular the following compounds having the INCI name:

Dimethicone/Vinyl Dimethicone Crosspolymer, such as "USG-105" and "USG-107A" of Shin-Etsu; "DC9506" and "DC9701" by Dow Corning, Dimethicone/Vinyl Dimethicone Crosspolymer (and) Dimethicone, such as "KSG-6" and "KSG-16" by the company Shin Etsu;

Dimethicone/Vinyl Dimethicone Crosspolymer (and) Cyclopentasiloxane, such as "KSG-15";

Cyclopentasiloxane (and) Dimethicone Crosspolymer, such as "DC9040", "DC9045" and "DC5930" from Dow Corning;

Dimethicone (and) Dimethicone Crosspolymer, such as "DC9041" from Dow Corning;

Dimethicone (and) Dimethicone Crosspolymer, such as "Dow Corning silicone elastomer EL-9240® Blend" from Dow Corning (mixture of polydimethylsiloxane with Reticulated hexadiene/polydimethylsiloxane (2 cSt));

C4-24 Alkyl Dimethicone/DivinylDimethicone Crosspolymer, such as Silk NuLastic Alzo AM by the company.

Examples of silicone elastomer dispersed in a linear silicone oil advantageously used in the invention, we may notably mention the following references:

Dimethicone/Vinyl Dimethicone Crosspolymer (and) Dimethicone, such as "KSG-6" and "KSG-16" by the company Shin Etsu;

Dimethicone (and) Dimethicone Crosspolymer, such as "DC9041" from Dow Corning; and Dimethicone (and) Dimethicone Crosspolymer, such as "Dow Corning silicone elastomer EL-9240® Blend" from Dow Corning (mixture of polydimethylsiloxane Reticulated by hexadiene/polydimethylsiloxane (2 cSt));

Diphenylsiloxy PHENYL trimethicone (and) Dimethicone (and) PHENYL VINYL DIMETHICONE CROSSPOLYMER (INCI name) such as KSG 18A marketed by Shin Etsu).

The organopolysiloxane elastomer particles can also be used in powder form, mention may be made of the powders sold under the name "Dow Corning 9505 Powder", "Dow Corning 9506 Powder" by Dow Corning, these powders have the INCI name: dimethicone/vinyl dimethicone crosspolymer. The organopolysiloxane powder may also be coated with silsesquioxane resin, as described for example in U.S. Pat. No. 5,538,793. Such elastomeric powders are sold under the names "KSP-100", "KSP-101", "KSP-102", "KSP-103", "KSP-104", "KSP-105" by the company Shin Etsu, and the INCI name: vinyl dimethicone/methicone silsesquioxane crosspolymer.

Examples of organopolysiloxane powders coated with silsesquioxane resin used advantageously according to the invention include in particular organopolysiloxane elastomers INCI name VINYL dimethicone/methicone SILSESQUIOANE CROSSPOLYMER as those sold under the brand name "KSP-100" of the Shin Etsu. As a preferred lipophilic gelling agent type organopolysiloxane elastomer that may especially be mentioned crosslinked organopolysiloxane elastomers chosen from Dimethicone Crosspolymer (INCI name), Dimethicone (and) Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name), VINYL dimethicone/methicone SILSESQUIOANE CROSSPOLYMER, diphenylsiloxy PHENYL trimethicone (and) Dimethicone (and) PHENYL VINYL DIMETHICONE CROSSPOLYMER (INCI name) and especially Dimethicone Crosspolymer (INCI name).

The organopolysiloxane is preferably present in a concentration from 0.2 to 5% by weight relative to the total weight of the composition.

Dispersant

Advantageously, a composition according to the invention may also comprise a dispersant.

Such a dispersant may be a surfactant, an oligomer, a polymer or a mixture of several thereof.

According to one particular embodiment, a dispersant in accordance with the invention is a surfactant.

Thickeners

Depending on the fluidity of the composition that it is desired to obtain, it is possible to incorporate one or more thickeners or gelling agents into a composition of the invention.

A thickener or gelling agent that is suitable for use in the invention may be hydrophilic, i.e. soluble or dispersible in water.

Hydrophilic gelling or thickening agents that may be mentioned in particular include water-soluble or water-dispersible thickening polymers. These polymers may be chosen especially from: modified or unmodified carboxyvinyl polymers, such as the products sold under the name Carbopol (CTFA name: Carbomer) by the company Goodrich; polyacrylates and polymethacrylates such as the products sold under the names Lubrajel and Norgel by the company Guardian or under the name Hispagel by the company Hispano Chimica; polyacrylamides; optionally crosslinked and/or neutralized 2-acrylamido-2-methylpropanesulfonic acid polymers and copolymers, for instance the poly(2-acrylamido-2-methylpropanesulfonic acid) sold by the company Clariant under the name Hostacerin AMPS® (CTFA name: ammonium polyacryldimethyltauramide); crosslinked anionic copolymers of acrylamide and of AMPS, which are in the form of a W/O emulsion, such as those sold under the name Sepigel 305 (CTFA name: Polyacrylamide/C13-14 Isoparaffin/Laureth-7) and under the name Simulgel 600 (CTFA name: Acrylamide/Sodium acryloyldimethyltaurate copolymer/Isohexadecane/Polysorbate 80) by the company SEPPIC; hydrophobic modified polymers of this type, of the copolymer of ammonium salt of 2-acrylamido-2-methylpropanesulphonic acid and of ethoxylated C12-C14 alkyl methacrylate (noncrosslinked copolymer obtained from ® Genapol LA-070 and from ® AMPS) (CTFA name: Ammonium Acryloyldimethyltaurate/ Laureth-7 Methacrylate Copolymer) sold under the name ® Aristoflex LNC by Clariant, and the crosslinked copolymer of ammonium salt of 2-acrylamido-2-methylpropanesulphonic acid and of ethoxylated (25 EO) stearyl methacrylate (copolymer which is preferably crosslinked with trimethylolpropane triacrylate and obtained from Genapol T-250 and from ®AMPS) (CTFA name: Ammonium Acryloyldimethyltaurate/Steareth-25 Methacrylate Crosspolymer) sold under the name ® Aristoflex HMS by Clariant; polysaccharide biopolymers, for instance xanthan gum, guar gum, carob gum, acacia gum, scleroglucans, chitin and chitosan derivatives, carrageenans, gellans, alginates, celluloses such as microcrystalline cellulose, carboxymethyl cellulose, hydroxymethyl cellulose and hydroxypropyl cellulose; and mixtures thereof.

According to one embodiment, a composition of the invention may comprise thickeners in an active material content from 0.01% to 40% by weight, especially from 0.1% to 20% by weight and in particular from 0.3% to 15% by weight relative to the total weight of the composition.

Active Agent

For a particular care application, a composition according to the invention may comprise at least one moisturizer (also known as a humectant).

Preferably, such moisturizer is glycerol.

The moisturizer(s) could be present in the composition in a content ranging from 0.1% to 15% by weight, especially from 0.5% to 10% by weight or even from 1% to 6% by weight, relative to the total weight of the said composition.

As other active agents that may be used in the composition of the invention, examples that may be mentioned include vitamins, such as vitamins A, C, E, B3, B5, K and their derivatives, in particular their esters, hyaluronic acid, sunscreens, urea and its hydroxylated derivatives, such as the N-(2-hydroxyethyl)urea sold under the name Hydrovance by National Starch; salicylic acid, 5-n-octanoyl salicylic acid or CAPRYLOYL SALICYLIC ACID sold under the trade name MEXORYL SAB®; C-BETA-D-XYLOPYRANOSIDE-2-HYDROXY-PROPANE in particular in solution at 30% in a mixture water/1,2-propanediol under the trade name MEXORYL BB®; sequestering agents, such as EDTA, and mixtures thereof.

Preferably, a composition of the invention comprises at least one active agent.

It is a matter of routine for those skilled in the art to adjust the nature and amount of the additives present in the compositions in accordance with the invention such that the desired cosmetic properties thereof are not thereby affected.

According to another embodiment, a composition of the invention may advantageously be in the form of a composition for caring for the skin in particular body, legs or the face, as anti-aging products, anti-winkles products, self-tanning products, suncare products, compositions for slimming, compositions for modulating the pigmentation.

According to one embodiment, a composition of the invention may advantageously be in the form of a composition for making up the skin and especially face, eyelids, around the eyes, cheeks. It may thus be a foundation, an eyeshadow, a cheekshadow.

According to another embodiment, a composition of the invention may advantageously be in the form of a lipcare product.

Such compositions are especially prepared according to the general knowledge of a person skilled in the art.

Assembly

The present invention also relates to a cosmetic assembly comprising:
- a container defining one or more compartments, said compartment being optionally closed by a closure member and optionally being non-sealing, and
- a composition for making up and/or care of the invention disposed within the compartment (s).

The compartment may for example be in the form of a box. The container may be a tube, a bootle. The assembly may also include an appropriate applicator as for example, a sponge, a buffer, a brush.

Throughout the description, including the claims, the term "comprising a" should be understood as being synonymous with "comprising at least one", unless otherwise specified.

The expressions "between . . . and . . . " and "ranging from . . . to . . . " should be understood as meaning limits included, unless otherwise specified.

The invention is illustrated in greater detail by the examples. Unless otherwise mentioned, the amounts indicated are expressed as weight percentages.

EXAMPLES

Reference is now made to the following examples, which together with the above descriptions illustrate some embodiments of the invention in a non limiting fashion.

Materials and Methods

Ethyl acetate was obtained from Gadot, Israel.

Magnesium stearate was obtained from FACI ASIA PACIFIC PTE Ltd.

Titanium oxide, which is also referred to herein throughout as titanium dioxide or $TiO_2$ RC402, was obtained from Sachtleben Chemie GmbH.

Bismuth oxychloride pre-dispersed 2-ethylhexyl hydroxystearate (marketed as Timiron® Liquid Silver) was obtained from Merck KGaA, Darmstadt, Germany.

Polyvinyl alcohol (PVA) as used was Mowiol 4-88, KSE solution 4%; Kuraray America, Inc., USA.

Cellulose acetate 398-10NF was obtained from Eastman, USA.

(Poly(ethyl acrylate-co-methyl methacrylate-co-trimethylammonium ethyl methacrylate chloride), EUDRAGIT® RS PO, was obtained from Evonik industries, Germany).

Size distribution of the microcapsules was determined using HORIBA LA300. Loose Bulk Density of the microcapsules was determined using USP-NF <616>.

Example 1

Preparation of PMMA Microcapsules Containing Bismuth Oxychloride Predispersed 2-ethylhexyl Hydroxystearate 1.1 Preparation of Organic Phase/Master Batch (MB)

An organic phase (herein referred to interchangeably as "master batch" (MB)) was prepared by gradually adding 10 grams of the wall-forming polymer poly(methyl methacrylate) (PMMA) under stirring (10 minutes), into 300 grams of ethyl acetate, heating the obtained mixture to 50° C. and stirring well until the mixture was homogeneous and transparent (about 20 minutes). The obtained polymer solution was cooled to 25° C. One gram of Magnesium Stearate (MgSt) was added to the solution under stirring for about 5 minutes. Ten grams of Titanium dioxide (TiO2) were then added to the solution under stirring for about 5 minutes and then the mixture was homogenized for about 8 minutes.

A mixture of bismuth oxychloride predispersed 2-ethylhexyl hydroxystearate (79 grams) was added to the previous suspension under stirring for about 5 minutes. A list of the components included in the prepared MB is presented in Table 1.

TABLE 1

| Master batch constituents | |
|---|---|
| Material | Loading for 100 grams MB |
| Poly(methyl methacrylate) | 10.0 |
| $TiO_2$ RC402 | 10.0 |
| Magnesium stearate | 1.0 |
| Bismuth oxychloride dispersed in 2-ethylhexyl hydroxystearate | 79.0 |
| Ethyl acetate | 300.0 |

1.2

1.3 Preparation of the Emulsion

An aqueous solution of 0.25% polyvinyl alcohol (PVA) was prepared by mixing water (1013 grams) with PVA 4% solution (68 grams). Ethyl acetate (120 grams) was added to the aqueous solution, and the master batch of step 1.1 above was thereafter gradually added into the ethyl acetate/water emulsion under stirring at about 400 RPM for 2 minutes. The ratio between the master batch and the emulsion (w/w) was ⅓. A list of the components included in the prepared emulsion is presented in Table 2.

TABLE 2

| Emulsion constituents | |
|---|---|
| Material | Loading (grams) |
| Water | 1013 |
| PVA (4% solution) | 68 |
| Ethyl Acetate | 120 |
| MB | 400 |

1.3 Extraction of the Organic Solvent

The extraction solution was composed of a mixture of 8775 grams water and 225 grams of PVA solution 4% (final concentration of PVA in the extraction solution was 0.10% PVA). The emulsion of step 1.2 above (1600 grams) was gradually added into the extraction solution in a 15 L pail under stirring at 150 RPM using a manual pump, and the obtained mixture was further stirred for additional 15 minutes. The resulting mixture was left to sediment for about 24 hours at 25° C. A list of the components included in extraction medium is presented in Table 3.

TABLE 3

| Extraction medium constituents | |
|---|---|
| Material | Loading (grams) |
| Emulsion | 1600 |
| Water | 8775 |
| 4% PVA solution | 225 |

1.4 Washing, Drying and Sifting of the Microcapsules

The microcapsules obtained in step 1.3 above were separated either by sedimentation or vacuum filtration, and then dried and sifted.

In the sedimentation procedure, the upper liquid phase from the pail was decanted and the remaining suspension was shaken and transferred to a drying vessel.

In the filtration procedure, the upper phase liquid was decanted from the pail, the remaining suspension was shaken and then filtered, and the sediment was rinsed on the filter with 400 ml water. The suspension was transferred to a drying vessel. In the drying stage, the microcapsules were freeze dried (lyophilized) for 48 hours. In the sifting stage, the dried microcapsules were sifted using automatic sifter "Ari j-Levy", Sifter MIC. 100. The sifted microcapsules were stored in an appropriate container at room temperature or in a refrigerator.

Example 2

Preparation of Cellulose Acetate Microcapsules Containing Bismuth Oxychloride Predispersed 2-ethylhexyl Hydroxystearate

2.1 Preparation of Organic Phase/Master Batch (MB) Stage

An organic phase (herein referred to interchangeably as "master batch" (MB)) was prepared by gradually adding 5 grams of the wall-forming polymer Cellulose Acetate 398-10NF (CA) under stirring (10 minutes), into 300 grams of ethyl acetate, and stirring the obtained mixture until the mixture was homogeneous and transparent (about 20 minutes). Thirty grams of Titanium dioxide (TiO2) were then added to the obtained solution under stirring for about 5 minutes and then the mixture was homogenized for about 8 minutes. A mixture of bismuth oxychloride predispersed in 2-ethylhexyl hydroxystearate (60 grams) was thereafter added to the suspension under stirring for about 5 minutes.

A list of the components included in the prepared MB is presented in Table 4.

TABLE 4

Master batch constituents

| Material | Loading for 100 grams MB |
|---|---|
| Cellulose acetate 398-10NF | 5.0 |
| TiO$_2$ RC402 | 35.0 |
| Bismuth oxychloride dispersed 2-ethylhexyl hydroxystearate | 60.0 |
| Ethyl acetate | 300.0 |

2.2 Preparation of the Emulsion

An aqueous solution of 0.4% polyvinyl alcohol (PVA) was prepared by mixing water (972 grams) with PVA 4% solution (108 grams). Ethyl acetate (120 grams) was added to the aqueous phase, and the master batch of step 3.1 above was thereafter gradually added into the ethyl acetate/water emulsion under stirring at about 400 RPM for 2 minutes. The ratio between the master batch and the emulsion (w/w) was ⅓. A list of the components included in the prepared emulsion is presented in Table 5.

TABLE 5

Emulsion constituents

| Material | Loading (grams) |
|---|---|
| Water | 972 |
| PVA (4% solution) | 108 |
| Ethyl Acetate | 120 |
| MB | 400 |

2.3 Extraction of the Organic Solvent

The extraction solution was composed of a mixture of 8550 grams water and 450 grams of PVA solution 4% (final concentration of PVA in the extraction fluid 0.20% PVA). The emulsion of step 3.2 above (1600 grams) was gradually added to the extraction solution in a 15 L pail under stirring at 150 RPM using a manual pump, and the obtained mixture was further stirred for additional 15 minutes. The resulting mixture was left to sediment for about 24 hours at 25° C. A list of the components included in the prepared extraction medium is presented in Table 6.

TABLE 6

Extraction medium constituents

| Material | Loading (grams) |
|---|---|
| Emulsion | 1600 |
| Water | 8550 |
| 4% PVA solution | 450 |

2.4 Washing, Drying and Sifting of the Microcapsules

The microcapsules obtained in step 3.3 above were separated either by sedimentation or vacuum filtration, dried and sifted, as described hereinabove, for Example 1.

Example 3

Preparation of EUDRAGIT® Microcapsules Containing Bismuth Oxychloride Predispersed 2-ethylhexyl Hydroxystearate

3.1 Preparation of Organic Phase/Master Batch (MB) Stage

An organic phase (herein referred to interchangeably as "master batch" (MB)) was prepared by gradually adding 10 grams of the wall-forming Poly(ethyl acrylate-co-methyl methacrylate-co-trimethylammonioethyl methacrylate chloride) (EUDRAGIT® RS PO) under stirring (10 minutes), into 300.0 grams of ethyl acetate, heating to 50° C. and stirring well until the mixture was homogeneous and transparent (about 20 minutes). The obtained polymer solution was cooled to 25° C. One gram of Magnesium Stearate (MgSt) was added to the solution under stirring for about 5 minutes. Then, bismuth oxychloride predispersed 2-ethylhexyl hydroxystearate (79 grams) was added to the suspension under stirring for about 5 minutes. The components of the MB are presented in Table 7.

TABLE 7

Master batch constituents

| Material | Loading for 100 grams MB |
|---|---|
| EUDRAGIT ® RS PO (Poly(ethyl acrylate-co-methyl methacrylate-co-trimethylammonioethyl methacrylate chloride) | 10.0 |

TABLE 7-continued

| Master batch constituents | |
| --- | --- |
| Material | Loading for 100 grams MB |
| Magnesium Stearate | 1.0 |
| Bismuth oxychloride dispersed in 2-ethylhexyl hydroxystearate | 79.0 |
| Ethyl acetate | 233 |

3.2 Preparation of the Emulsion

An aqueous solution of 0.25% polyvinyl alcohol (PVA) was prepared by mixing water (844 grams) with PVA 4% solution (56 grams). Ethyl acetate (100 grams) was added to the water phase. Ten grams of Titanium dioxide (TiO2) was added to previous step under stirring for about 5 minutes and then the mixture was homogenized for about 8 minutes and then the master batch of step 4.1 above was gradually added into the ethyl acetate/water emulsion under stirring at about 400 RPM for 2 minutes. The ratio between the master batch and the emulsion (w/w) was ⅓. The components of the emulsion are presented in Table 8.

TABLE 8

| Emulsion constituents | |
| --- | --- |
| Material | Loading (grams) |
| Water | 844 |
| PVA (4% solution) | 56 |
| Ethyl Acetate | 100 |
| TiO$_2$ RC402 | 10 |
| MB | 323 |

3.3 Extraction of the Organic Solvent

The extraction fluid was composed of a mixture of 6923 grams water and 178 grams of PVA solution 4% (final concentration of PVA in the extraction fluid 0.10% PVA). The emulsion of step 4.2 above (1333 grams) was gradually added into the extraction fluid in a 15 L pail under stirring at 150 RPM using a manual pump, and was further stirred for additional 15 minutes. The resulting mixture was left to sediment for about 24 hours at 25° C. The components of the extraction medium are presented in Table 9.

TABLE 9

| Extraction medium constituents | |
| --- | --- |
| Material | Loading (grams) |
| Emulsion | 1333 |
| Water | 6923 |
| 4% PVA solution | 178 |

3.4 Washing, Drying and Sifting of the Microcapsules

The microcapsules obtained in step 3.3 above were separated either by sedimentation or vacuum filtration, dried and sifted, as described hereinabove, for Example 1.

Example 4

Preparation of PMMA/MA Microcapsules Containing Bismuth Oxychloride Predispersed 2-ethylhexyl Hydroxystearate 4.1 Preparation of Organic Phase/Master Batch (MB) Stage An organic phase (herein referred to interchangeably as "master batch" (MB)) was prepared by gradually adding 10 grams of the wall-forming polymer Poly(methacrylic acid-co-methyl methacrylate) (PMMA/MA) under stirring (10 minutes), into 300.0 grams of ethyl acetate, heating to 50° C. and stirring well until the mixture was homogeneous and transparent (about 20 minutes). The obtained polymer solution was cooled to 25° C. One gram of Magnesium Stearate (MgSt) was added to the solution under stirring for about 5 minutes. Ten grams of Titanium dioxide (TiO2) were thereafter added under stirring for about 5 minutes and then the mixture was homogenized for about 8 minutes. Thereafter, bismuth oxychloride predispersed 2-ethylhexyl hydroxystearate (79 grams) was added to the suspension under stirring for about 5 minutes. The components of the MB are presented in Table 10.

TABLE 10

| Master batch constituents | |
| --- | --- |
| Material | Loading for 100 grams MB |
| Poly(methacrylic acid-co-methyl methacrylate) (PMMA/MA) | 10.0 |
| TiO$_2$ RC402 | 10.0 |
| Magnesium stearate | 1.0 |
| Bismuth oxychloride dispersed in 2-ethylhexyl hydroxystearate | 79.0 |
| Ethyl acetate | 300.0 |

4.2 Preparation of the Eulsion

An aqueous solution of 0.25% polyvinyl alcohol (PVA) was prepared by mixing water (1013 grams) with PVA 4% solution (68 grams). Ethyl acetate (120 grams) was added to the water phase, and then the master batch of step 1.1 above was gradually added into the ethyl acetate/water emulsion under stirring at about 400 RPM for 2 minutes. The ratio between the master batch and the emulsion (w/w) was ⅓. The components of the emulsion are presented in Table 11.

TABLE 11

| Emulsion constituents | |
| --- | --- |
| Material | Loading (grams) |
| Water | 1013 |
| PVA (KSE 4% solution) | 68 |
| Ethyl Acetate | 120 |
| MB | 400 |

4.3 Extraction of the Organic Solvent

The extraction fluid was composed of a mixture of 8775 grams water and 225 grams of PVA solution 4% (final concentration of PVA in the extraction fluid 0.10% PVA). The emulsion of step 1.2 above (1600 grams) was gradually added into the extraction fluid in a 15 L pail under stirring at 150 RPM using a manual pump, and was further stirred for additional 15 minutes. The resulting mixture was left to sediment for about 24 hours at 25° C. The components of the extraction medium are presented in Table 12.

TABLE 12

| Extraction medium constituents | |
| --- | --- |
| Material | Loading (grams) |
| Emulsion | 1600 |
| Water | 8775 |
| 4% PVA solution | 225 |

4.4 Washing, Drying and Sifting of the Microcapsules

The microcapsules obtained in step 4.3 above were separated either by sedimentation or vacuum filtration, dried and sifted, as described hereinabove, for Example 1.

Example 5

Preparation of EUDRAGIT® Microcapsules Containing Bismuth Oxychloride Predispersed 2-ethylhexyl Hydroxystearate 5.1 Preparation of Organic Phase/Master Batch (MB) Stage An organic phase (herein referred to interchangeably as "master batch" (MB)) was prepared by gradually adding 10 grams of the wall-forming polymer Poly(ethyl acrylate-co-methyl methacrylate-co-trimethylammonioethyl methacrylate chloride) (EUDRAGIT® RS PO) under stirring (10 minutes), into 185.7 grams of ethyl acetate, heating to 50° C. and stirring well until the mixture was homogeneous and transparent (about 20 minutes). The obtained polymer solution was cooled to 25° C. Ten grams of Triethyl Citrate were added to the solution under stirring for about 5 minutes. Eighty grams of bismuth oxychloride (BiClO) were thereafter added to the mixture under stirring for about 5 minutes and then the mixture was homogenized for about 8 minutes. The components of the MB are presented in Table 13.

TABLE 13

Master batch constituents

| Material | Loading for 100 grams MB |
|---|---|
| EUDRAGIT ® RS PO (Poly(ethyl acrylate-co-methyl methacrylate-co-trimethylammonioethyl methacrylate chloride) | 10.0 |
| Triethyl Citrate | 10.0 |
| Bismuth oxychloride dispersed in 2-ethylhexyl hydroxystearate | 80.0 |
| Ethyl acetate | 185.7 |

5.2 Preparation of the Emulsion

An aqueous solution of 0.25% polyvinyl alcohol (PVA) was prepared by mixing water (723.2 grams) with PVA 4% solution (48.2 grams). Ethyl acetate (85.7 grams) was added to the water phase, and then the master batch of step 6.1 above was gradually added into the ethyl acetate/water emulsion under stirring at about 400 RPM for 10 minutes. The ratio between the master batch and the emulsion (w/w) was 1:3. The components of the emulsion are presented in Table 14.

TABLE 14

Emulsion constituents

| Material | Loading (grams) |
|---|---|
| Water | 723.2 |
| PVA (4% solution) | 48.2 |
| Ethyl Acetate | 85.7 |
| MB | 285.7 |

5.3 Extraction of the Organic Solvent

The extraction fluid was composed of a mixture of 5599 grams water and 144 grams of PVA solution 4% (final concentration of PVA in the extraction fluid 0.10% PVA). The emulsion of step 6.2 above (1449.2 grams) was gradually added into the extraction fluid in a 15 L pail under stirring at 150 RPM using a manual pump, and was further stirred for additional 15 minutes. The resulting mixture was left to sediment for about 24 hours at 25° C. The components of the extraction medium are presented in Table 15.

TABLE 15

Extraction medium constituents

| Material | Loading (grams) |
|---|---|
| Emulsion | 1449.2 |
| Water | 5599 |
| 4% PVA solution | 144 |

5.4 Washing, Drying and Sifting of the Microcapsules

The microcapsules obtained in step 5.3 above were separated either by sedimentation or vacuum filtration, dried and sifted, as described hereinabove, for Example 1.

Example 6

Characterization

Size Distribution:

The size distribution of the microcapsules obtained in Examples 1-5 was measured and the obtained data are indicated below.

Herein throughout, a "mean" diameter means an average size of the microcapsules. The size of the microcapsules may be measured by a Laser distribution size method and particularly by measuring the values D[50] and D[90]. D50 means the size of which 50% of the microcapsules do not exceed, and D90 means the size of which 90% of the microcapsules do not exceed.

The diameter of the microcapsules obtains as described in Example 1 is in the range of from about 3 microns to about 600 microns, with the mean diameter being about 175 microns, the D50 of the microcapsules being about 155 microns, and the D90 of the microcapsules being about 320 microns.

The diameter of the microcapsules obtains as described in Example 3 is in the range of from about 3 microns to about 500 microns, with the mean diameter being about 120 microns, the D50 of the microcapsules being about 96 microns, and the D90 of the microcapsules being about 237 microns.

The diameter of the microcapsules obtains as described in Example 4 is in the range of from about 3 microns to about 400 microns, with the mean diameter being about 120 microns, the D50 of the microcapsules being about 106 microns, and the D90 of the microcapsules being about 195 microns.

The diameter of the microcapsules obtains as described in Example 5 is in the range of from about 3 microns to about 250 microns, with the mean diameter being about 120 microns, the D50 of the microcapsules being about 96 microns, and the D90 of the microcapsules being about 237 microns.

Loose Bulk Density:

The loose bulk density of the microcapsules obtained in Example 1 was determined as ranging from about 300 to about 450 grams/liter (from about 0.30 to about 0.45 gram/$cm^3$), or from about 300 to about 380 grams/liter (from about 0.30 to about 0.38 gram/$cm^3$) or from about 300 to about 340 grams/liter (from about 0.30 to about 0.4 gram/$cm^3$).

The loose bulk density of the microcapsules obtained in Example 2 was determined as ranging from about 360 to about 460 grams/liter (from about 0.36 to about 0.46 gram/cm³), or from about 380 to 440 grams/liter (from about 0.38 to about 0.44 gram/cm³), or from about 400 to 420 grams/liter (from about 0.40 to about 0.42 gram/cm³).

The loose bulk density of the microcapsules obtained in Example 3 was determined as ranging from about 140 to about 360 grams/liter (from about 0.14 to about 0.36 gram/cm³), or from about 200 to 300 grams/liter (from about 0.20 to about 0.30 gram/cm³), or from about 240 to about 260 grams/liter (from about 0.24 to about 0.26 gram/cm3).

The loose bulk density of the microcapsules obtained in Example 5 was determined as ranging from about 420 to about 560 grams/liter (from about 0.42 to about 0.56 gram/cm³), or from about 450 to about 530 grams/liter (from about 0.45 to about 0.53 gram/cm³), or from about 480 to about 500 grams/liter (from about 0.48 to about 0.50 gram/cm³).

Masking:

Quantitative measurements of the masking effect provided by encapsulating bismuth oxychloride, the X-Rite measurement technique using the CIE Color Systems (based on the CIE L*a*b* color scale, wherein L* defines lightness, a* denotes the red/green value and b* the yellow/blue value) was used. The standard illuminant applied for these measurements was daylight.

Quantitative values were obtained by integrating values/data measured for three visual elements of color: hue (namely, how we perceive an object's color), chroma (the vividness or dullness of a color namely, how close the color is to either gray or the pure hue), and degree of lightness (namely classifying whether a color is light or dark).

Table 16 below presents the shift in lightness on the lightness scale L* of the present microcapsules relative to the bismuth oxychloride-containing raw material Timiron® Liquid Silver (DL*). The positive DL* values presented in Table XXX denote a shift on the lightness scale in the direction of substantially lighter, brighter color for the microcapsules of the invention compared to the raw material, which is indicative of the masking effect.

TABLE 16

| Example No. | DL* relative to Timiron ® Liquid Silver Raw material |
|---|---|
| 1 | 8.45 |
| 2 | 5.71 |
| 3 | 9.96 |
| 5 | 13.47 |

Light Reflectance:

Light reflectance is measured using polarized goniophotometer system with a halogen lamp. Both input and detected light are polarized. The incident light angle is 45° and a convergent angle ranges over 20-75°, with a moving detector. The detection polarizer can be rotated to collect either parallel or perpendicular polarized light. Each quantity of light can be calculated from the quantity of parallel filtered and vertically filtered light.

The quantity of internally reflected light:

Iinternally reflected light=2×Ivertical

The quantity of surface-reflected light:

Isurface-reflected light=Iparallel−Ivertical

The quantity of totally reflected light:

Itotal=Iinternally+Isurface=Iparallel+Ivertical

Icrossed: the quantity of light passing through the crossed polarized filters.

Iparallel: the quantity of light passing through the parallel polarized filters.

Exemple 7

Tinted Serum (Aqueous Dispersion)

| Ingredients | Amounts % by weight |
|---|---|
| Octyldodecanol | 0.44 |
| Iron oxides | 3.56 |
| Titanium Dioxide | 8.94 |
| Denaturated Alcohol | 4.38 |
| Water | qsp 100 |
| Disodium EDTA | 0.09 |
| PEG-20 Methyl Glucose Sesquistearate | 0.09 |
| Sodium Hyaluronate | 0.35 |
| Glycerin | 4.38 |
| Dimethicone | 0.88 |
| Preservatives | 0.7 |
| Microcapsules containing Bismuth Oxychloride oily dispersion of Exemple 1 | 3.0 |
| PEG-60 Hydrogenated Castor Oil | 0.01 |

The tinted serum led to a natural glow, good sensorial propertiues as freshness, smoothness, non-greasy feeling and without observing a too pearly shine in the mass.

The invention claimed is:

1. A composition for caring for and/or making up keratin materials comprising, in a physiologically acceptable medium:
   a) one aqueous phase; and
   b) microcapsules comprising:
      an inner core comprising a dispersion of at least one reflective agent in at least one oil, wherein the at least one reflective agent is bismuth oxychloride and the at least one oil is a non-volatile polar hydrocarbon-based oil selected from the group consisting of 2-ethylhexyl hydroxystearate, ethylhexyl ethylhexanoate, and mixtures thereof, and
      at least one outer shell formed of a wall-forming polymeric material surrounding the core, the outer shell comprising
         i) at least one wall-forming polymer, and
         ii) optionally at least one selected from the group consisting of plasticizer, opaque substance, and fatty acid salt.

2. The composition according to claim 1, wherein an amount of the reflective agent ranges from 50% to 90% by weight based on a total weight of the dispersion.

3. The composition according to claim 1, wherein a weight ratio of the reflective agent particles to the oil(s) ranges from 1.5/1 to 5/1.

4. The composition according to claim 1, wherein the dispersion of reflective agent in the at least one oil is a dispersion of bismuth oxychloride in ethylhexyl hydroxystearate.

5. The composition according to claim 1, wherein the wall-forming polymer forming the outer shell(s) is selected from a polyacrylate, a polymethacrylate, a cellulose ether or ester, or any combination thereof.

6. The composition according to claim 5, wherein the wall-forming polymer is selected from the group consisting of poly(methyl methacrylate) (PMMA), poly(methyl methacrylate)-co-(methacrylic acid) (PMMA/MA), an acrylate/ammonium methacrylate copolymer, and cellulose acetate.

7. The composition according to claim 1, wherein the outer shell of the microcapsules comprises an opaque substance, the opaque substance being selected from $TiO_2$, zinc oxide, alumina, boron nitride, talc, mica and any combination thereof.

8. The composition according to claim 1, wherein the outer shell of the microcapsules comprises a fatty acid salt, the fatty acid salt being magnesium stearate.

9. The composition according to claim 1, wherein the microcapsules comprise
the inner core in an amount within a range of from 20% to 90% by weight relative to a total weight of the microcapsule; and
the wall-forming polymer(s) of the outer shell within a range of from 5% to 30% by weight relative to the total weight of the microcapsule; and
optionally, the opaque substance(s) in the outer shell in an amount ranging from 1% to 50% by weight, relative to the total weight of the microcapsule; and/or
optionally, the fatty acid salt in the outer shell in an amount ranging from 0.05% to 5% by weight, relative to the total weight of the microcapsule; and/or
optionally, the plasticizer(s) in the outer shell in an amount ranging from 0.5% to about 30% by weight, preferably from 0.5% to 20% by weight, more preferably from 1.0% to 20% by weight, relative to the total weight of the microcapsule.

10. The composition according to claim 1, wherein the microcapsules are single-layer microcapsules.

11. The composition according to claim 10, wherein the single-layer microcapsules comprise:
the inner core comprising bismuth oxychloride dispersed in 2-ethylhexyl hydroxystearate in an amount from 60 to 80% by weight, and
the outer shell comprising magnesium stearate in an amount ranging from 1.0% to 2.0% by weight, $TiO_2$ in an amount ranging from 1% to 20% by weight, and, as a wall-forming polymer, PMMA, in an amount ranging from 5% to 20% by weight relative to a total weight of the microcapsule.

12. The composition according to claim 10, wherein the single-layer microcapsules comprise:
the inner core comprising bismuth oxychloride dispersed in 2-ethylhexyl hydroxystearate in an amount from 60 to 80% by weight, and
the outer shell comprising $TiO_2$ in an amount ranging from 10% to 50% by weight, and, as a wall-forming polymer, ethyl cellulose, in an amount ranging from 1% to 10% by weight relative to a total weight of the microcapsule, wherein the outer shell does not comprise magnesium stearate.

13. The composition according to claim 10, wherein the single-layer microcapsules comprise:
the inner core comprising bismuth oxychloride dispersed in 2-ethylhexyl hydroxystearate in an amount from 60 to 80% by weight, and
the outer shell comprising magnesium stearate in an amount ranging from 1.0% to 2.0% by weight, $TiO_2$ in an amount ranging from 1% to 20% by weight, and, as a wall-forming polymer, poly(ethyl acrylate)-co-methyl methacrylate-co-trimethyl ammonium ethyl methacrylate chloride, in an amount ranging from 5% to 20% by weight relative to a total weight of the microcapsule.

14. The composition according to claim 10, wherein the single-layer microcapsules comprise:
the inner core comprising bismuth oxychloride dispersed in 2-ethylhexyl hydroxystearate in an amount ranging from 60% to 80% by weight, and
the outer shell comprising magnesium stearate in an amount ranging from 1.0% to 2.0% by weight, $TiO_2$ in an amount ranging from 1% to 20% by weight, and, as a wall-forming polymer, PMMA/MA, in an amount ranging from 5% to 20% by weight relative to a total weight of the microcapsule.

15. The composition according to claim 10, wherein the single-layer microcapsules comprise:
the inner core comprising bismuth oxychloride dispersed in 2-ethylhexyl hydroxystearate in an amount ranging from 60% to 80% by weight, and
the outer shell comprising a plasticizer, in an amount ranging from 1% to 20% by weight, and, as a wall-forming material, poly(ethyl acrylate)-co-methyl methacrylate-co-trimethyl ammonium ethyl methacrylate chloride, in an amount ranging from 5% to 20% by weight relative to a total weight of the microcapsule, wherein the outer shell does not comprise magnesium stearate nor $TiO_2$.

16. The composition according to claim 1, further comprising at least one coloring agent.

17. The composition according to claim 1, further comprising at least one mono-alcohol comprising from 2 to 8 carbon atoms.

18. The composition according to claim 1, further comprising at least one filler.

19. The composition according to claim 1, further comprising at least one non-emulsifying organopolysiloxane elastomer.

20. A cosmetic process for caring for and/or making up keratinic materials, comprising applying on said keratinic materials the composition as defined in claim 1.

* * * * *